United States Patent
Biddle

(10) Patent No.: US 9,568,406 B2
(45) Date of Patent: Feb. 14, 2017

(54) PORTABLE BRINELL HARDNESS TESTER WITH STENTED THROUGH BORE PUMPING CHAMBER

(71) Applicant: Ernest L. Biddle, Bryn Mawr, PA (US)

(72) Inventor: Ernest L. Biddle, Bryn Mawr, PA (US)

(73) Assignee: King Tester Corporation, Phoenixville, PA (US)

( * ) Notice: Subject to any disclaimer, the term of this patent is extended or adjusted under 35 U.S.C. 154(b) by 0 days.

(21) Appl. No.: 14/836,160

(22) Filed: Aug. 26, 2015

(65) Prior Publication Data

US 2015/0362416 A1    Dec. 17, 2015

Related U.S. Application Data

(63) Continuation-in-part of application No. 14/266,186, filed on Apr. 30, 2014, which is a continuation of application No. 14/051,820, filed on Oct. 11, 2013, which is a continuation of application No. 13/222,290, filed on Aug. 31, 2011, now Pat. No. 8,590,367.

(51) Int. Cl.
*G01N 3/40* (2006.01)
*G01N 3/42* (2006.01)
*G01D 7/00* (2006.01)

(52) U.S. Cl.
CPC ........ *G01N 3/40* (2013.01); *G01N 3/42* (2013.01); *G01D 7/00* (2013.01); *G01N 2203/0048* (2013.01); *G01N 2203/0098* (2013.01); *Y10T 137/7837* (2015.04); *Y10T 137/7922* (2015.04); *Y10T 137/7928* (2015.04)

(58) Field of Classification Search
CPC .............. G01N 3/40; G01N 3/42; G01D 7/00
See application file for complete search history.

(56) References Cited

U.S. PATENT DOCUMENTS

| | | |
|---|---|---|
| D31,361 S | 8/1899 | Ball |
| D34,213 S | 3/1901 | Baxter |
| 827,846 A | 8/1906 | Bowser et al. |
| 1,209,350 A | 12/1916 | Steiner |

(Continued)

FOREIGN PATENT DOCUMENTS

| | | |
|---|---|---|
| DE | 2357755 | 6/1974 |
| DE | 2751095 | 3/1979 |

OTHER PUBLICATIONS

International Search Report for PCT/US2012/052979, dated Dec. 26, 2012.

(Continued)

*Primary Examiner* — Hezron E Williams
*Assistant Examiner* — David Z Huang
(74) *Attorney, Agent, or Firm* — Fox Rothschild LLP

(57) ABSTRACT

A portable Brinell metal hardness tester has a test head mounted in a carriage, movable vertically along elevating screws, and includes a reciprocable pumping rack movable in response to manual movement of a pumping lever, for pumping hydraulic fluid into a passageway of the tester to increase hydraulic fluid pressure in the tester to a level required for metal hardness testing; and a stent located in the passageway for permitting pumped hydraulic fluid to flow through the passageway into a test head portion of the tester to apply hydraulic fluid to the ball contacting the test piece and interferingly stopping the rack upon movement of the rack into the passageway by a preselected amount.

16 Claims, 18 Drawing Sheets

(56) References Cited

U.S. PATENT DOCUMENTS

| | | |
|---|---|---|
| 1,232,782 A | 7/1917 | Field |
| 1,354,218 A | 9/1920 | Schneider |
| 1,384,389 A | 7/1921 | Johnson |
| 1,431,832 A | 10/1922 | Mills et al. |
| 1,646,195 A | 10/1927 | German |
| D78,990 S | 7/1929 | Stevenson |
| 1,770,045 A | 7/1930 | Shore et al. |
| 1,973,333 A | 9/1934 | Craemer |
| 2,029,066 A | 1/1936 | Geppert |
| 2,203,129 A | 6/1940 | Campbell et al. |
| 2,297,778 A | 10/1942 | Knerr et al. |
| 2,319,208 A | 5/1943 | Clark |
| 2,337,573 A | 12/1943 | Schultz |
| 2,391,394 A | 12/1945 | Cogbill |
| 2,418,916 A | 4/1947 | Weaver |
| 2,448,486 A | 8/1948 | Chester |
| 2,466,567 A | 4/1949 | Williams |
| 2,532,027 A | 11/1950 | Maddox |
| 2,535,830 A | 12/1950 | Beck |
| D168,385 S | 12/1952 | Watson |
| 2,643,544 A | 6/1953 | Chester |
| 2,693,698 A | 11/1954 | Scott |
| D178,060 S | 6/1956 | Karol |
| 2,804,769 A | 9/1957 | Clark, Sr. |
| 2,835,127 A | 5/1958 | Scott |
| 2,839,917 A | 6/1958 | Webster |
| 2,956,432 A | 10/1960 | Henrikson |
| 2,966,083 A | 12/1960 | North |
| 2,976,723 A | 3/1961 | Eddy |
| 3,029,631 A * | 4/1962 | Borgersen ............... G01N 3/42 73/81 |
| 3,083,598 A | 4/1963 | Kinnison |
| 3,102,417 A | 9/1963 | Chambers |
| 3,128,621 A | 4/1964 | Scott |
| 3,129,582 A * | 4/1964 | Borgersen ............... G01N 3/42 73/81 |
| 3,138,951 A | 6/1964 | Scott |
| 3,156,143 A | 11/1964 | Wolf |
| D200,799 S | 4/1965 | Dickman |
| D203,933 S | 3/1966 | Griffith |
| 3,247,824 A | 4/1966 | Rodgers |
| 3,309,916 A | 3/1967 | Pearson |
| 3,370,421 A | 2/1968 | Piper |
| 3,478,568 A | 11/1969 | Borgersen |
| 3,486,373 A | 12/1969 | Scott |
| D219,861 S | 2/1971 | Coffman |
| D223,174 S | 3/1972 | Pettavel |
| 3,728,551 A | 4/1973 | Culver et al. |
| 3,754,436 A | 8/1973 | Saxton |
| 3,815,125 A | 6/1974 | May et al. |
| 3,908,489 A | 9/1975 | Yamamoto et al. |
| 3,980,066 A | 9/1976 | Hollins |
| 4,036,048 A | 7/1977 | Webster |
| 4,075,478 A | 2/1978 | Walker |
| 4,094,188 A | 6/1978 | Bellouin et al. |
| 4,144,007 A | 3/1979 | Singh |
| 4,147,052 A | 4/1979 | Tsujiuchi et al. |
| 4,193,199 A | 3/1980 | Whiteley et al. |
| 4,312,220 A | 1/1982 | Borgersen et al. |
| 4,361,034 A | 11/1982 | Borgersen et al. |
| 4,562,758 A | 1/1986 | Stirling |
| D283,599 S | 4/1986 | Biddle et al. |
| 4,945,490 A | 7/1990 | Biddle, Jr. et al. |
| 5,388,486 A | 2/1995 | Ruzicka et al. |
| D369,968 S | 5/1996 | Decursu et al. |
| D387,640 S | 12/1997 | Von Fange |
| D406,993 S | 3/1999 | Jones |
| D420,927 S | 2/2000 | Yano |
| 6,050,165 A | 4/2000 | Hall |
| 6,408,829 B1 * | 6/2002 | Lei ............ F02M 45/04 123/300 |
| 6,516,689 B1 | 2/2003 | Bates |
| 6,837,266 B2 | 1/2005 | Fredrickson et al. |
| 6,908,113 B2 | 6/2005 | Chaduc et al. |
| 7,000,505 B2 | 2/2006 | Hsien |
| D661,969 S | 6/2012 | Biddle |
| 8,590,367 B2 * | 11/2013 | Biddle ............ G01N 3/42 137/539.5 |
| 2006/0214789 A1 | 9/2006 | Posamentier et al. |
| 2008/0041470 A1 | 2/2008 | Golan et al. |
| 2008/0078460 A1 | 4/2008 | Roper et al. |
| 2008/0083460 A1 | 4/2008 | Yang |
| 2010/0021349 A1 * | 1/2010 | Boehm ............ B01L 3/0206 422/400 |
| 2013/0291715 A1 * | 11/2013 | Carcaterra ............ G01V 1/135 92/61 |

OTHER PUBLICATIONS

Written Opinion for PCT/US2012/052979, dated Dec. 26, 2012.
Nov. 19, 2013 Screen Print from http://www.wilson-hardness.com/Products/TestBlocksandIndenters/BrinellTestBlocksandIndenters.aspx.

* cited by examiner

PORTABLE BRINELL HARDNESS TESTER WITH STENTED THROUGH BORE PUMPING CHAMBER

CROSS-REFERENCE TO RELATED PATENT APPLICATIONS

This patent application is a 35 USC 120 continuation-in-part of co-pending U.S. patent application Ser. No. 14/266,186 filed 30 Apr. 2014, entitled "Portable Brinell Hardness Tester", which in turn is a 35 USC 120 continuation of co-pending U.S. patent application Ser. No. 14/051,820, which is also entitled "Portable Brinell Hardness Tester", filed 11 Oct. 2013, which in turn is a 35 USC 120 continuation of U.S. patent application Ser. No. 13/222,290, also entitled "Portable Brinell Hardness Tester", filed 31 Aug. 2011 and issued 26 Nov. 2013 as U.S. Pat. No. 8,590,367. The priority of both the '186 and '820 applications and the '367 patent is hereby claimed and the disclosures of both the '186 and '820 applications and the '367 patent are hereby incorporated by reference to the extent permissible under applicable law.

BACKGROUND OF THE INVENTION

Field of the Invention

This invention relates generally to metal hardness testers and specifically to portable metal hardness testers using the Brinell method of hardness testing.

Description of the Prior Art

The portable Brinell metal hardness tester, as invented by the late Roland D. Borgersen, as disclosed and claimed in U.S. Pat. No. 3,129,582 has, over the past fifty years, become the standard of the world for portable Brinell metal hardness testers. The U.S. Pat. No. 3,129,582 tester, as manufactured and sold by the King Tester Corporation, the assignee of the '582 patent, has been and is commercially successful and has been copied prolifically since the '582 patent expired. Portable metal hardness testers that appear to be bolt-for-bolt copies of the tester disclosed and claimed in U.S. Pat. No. 3,129,582, but which are actually poor quality copies of the '582 apparatus, are readily available all over the world. One need only to perform a Google search for "portable Brinell metal hardness tester" to find literally hundreds of sources of supply of machines that are visually indistinguishable from the tester disclosed in U.S. Pat. No. 3,129,582.

The same commercial success and third party copying is true respecting the improved portable Brinell metal hardness tester invented by the late Mr. Borgersen and two collaborators as disclosed and claimed in the U.S. Pat. No. 4,361,034, also assigned to the King Tester Corporation.

While the portable Brinell metal hardness testers disclosed and claimed in U.S. Pat. Nos. 3,129,582 and 4,361,034 have been commercially highly successful, improvements can always be made even in the most successful of products, including the '582 and '034 portable Brinell metal hardness testers.

An occasional annoyance when calibrating the tester or when changing the hydraulic fluid in the portable Brinell metal hardness tester of the type disclosed in U.S. Pat. Nos. 3,129,582 and 4,361,034 is leakage of hydraulic fluid occurring during the calibration or oil change process. The process is messy in that hydraulic fluid, namely oil, inevitably escapes. Moreover, there is always risk of contamination of the hydraulic fluid in the course of the changing of the fluid and/or calibration of the tester.

Another problem arising occasionally is that overzealous technicians, in the course of manually pumping the tester while making a test, inadvertently or perhaps sometimes semi-intentionally pull the pump handle through a greater range of angular travel than for which the tester was designed, thereby either breaking the pump handle or damaging the internal gears of the oil pump within the tester. In either case, the tester is rendered inoperative until it is repaired.

A third problem in using the testers of the '582 and '034 patents is that of technician tampering with the tester once the tester has been calibrated. Neither the '582 tester nor the '034 tester has any means to detect tampering once the tester has been calibrated.

Yet another minor problem with the testers of '582 and '034 patents is that the handle for the pressure release valve is difficult to grasp. Sometimes it may be necessary for the operator to rapidly release the hydraulic pressure within the tester. The handle for the pressure release valve in both the '582 and '034 patent testers is difficult to grasp by an adult, making quick action in opening the pressure release valve difficult.

SUMMARY OF THE INVENTION

The invention(s) disclosed in parent application U.S. Ser. No. 13/222,290 provides substantial improvements to portable Brinell metal hardness testers disclosed in the U.S. Pat. Nos. 3,129,582 and 4,361,034 by facilitating rapid manual release of hydraulic pressure when required; prevention of breakage of the hydraulic pump mechanism; easier, faster and cleaner calibration and hydraulic oil change; and detection of tampering with the tester, particularly of the calibration setting for the tester.

The invention(s) disclosed in parent application U.S. Ser. No. 13/222,290 facilitate quick adjustment and calibration of portable Brinell metal hardness testers of the type disclosed in U.S. Pat. Nos. 3,129,582 and 4,361,034, without contaminating the hydraulic fluid, typically oil, in the tester. Using the invention(s) disclosed in parent application U.S. Ser. No. 13/222,290, the loads involved may be changed quickly without contaminating oil in the tester.

The invention(s) disclosed in parent application U.S. Ser. No. 13/222,290 facilitate faster adjustment of the tester and more precise adjustment of the tester than was previously possible when calibrating by either direct or indirect verification, using methodologies disclosed in the American Society for Testing Materials Publication E10 for Brinell tester calibration.

Prior to the invention(s) disclosed in parent application U.S. Ser. No. 13/222,290, when calibrating or changing oil and recalibrating a portable Brinell metal hardness tester of the type disclosed in U.S. Pat. Nos. 3,129,582 and 4,361,034, one had to perform the following steps: (i) remove the socket head screw over the pop-off pressure relief valve located within an internal bore of the machine test head; (ii) place the test block or load cell on the tester anvil and begin the test procedure; (iii) with a screwdriver, adjust the load by turning a calibrating nut either right or left to adjust the load; and (iv) when finished calibrating, reinstall and tighten the socket head screw and copper gaskets of the pressure relief valve so that oil could not escape. This process was messy and allowed contamination of the hydraulic fluid, namely oil, used in the hydraulic portion of the tester.

In one aspect, the invention(s) disclosed in parent application U.S. Ser. No. 13/222,290 provide a pressure relief valve with an external cap that is removable by hand whereupon the tester may be adjusted by turning an extended hex head screw. The pressure relief valve external cap protects the external calibrating hex head screw from damage and prevents leakage of hydraulic fluid to the tester exterior from the pressure release valve.

In another one of its aspects, the invention(s) disclosed in parent application U.S. Ser. No. 13/222,290 provide a portable metal hardness tester having a test head for applying preselected force to a test piece by application of preferably manually-pumped hydraulic fluid into a ram pressure chamber to move a ram cylinder within the test head towards the test piece, where the test head includes an externally adjustable pressure relief valve residing within a threaded passageway extending from the test head exterior into contact with the hydraulic fluid.

The pressure relief valve disclosed in parent application U.S. Ser. No. 13/222,290 preferably includes a stem having a circular head adapted to fit sealingly against a seat formed in a passageway in the test head, with the passageway communicating with the hydraulic fluid within the test head and connecting to the ram pressure chamber. The pressure relief valve preferably further includes a shaft having a first end integrally formed with and extending coaxially from the circular head. The pressure relief valve preferably yet further includes a spring for biasing the stem against the seat, with the spring residing slidably about the shaft.

The pressure relief valve preferably yet further includes an annular cap slidably receiving a second end of the shaft through a central aperture, with the spring contacting the cap outboard of the central aperture. The pressure relief valve preferably yet further includes an internal member having a first end with a circular recess adapted for receiving the annular cap therewithin, with the first end being externally threaded for engagement with corresponding threads formed in the passageway. The internal member preferably further includes a central shaft portion and a second end having an axially facing receptacle for receiving a hexagonal wrench therewithin for manual rotation of the intermediate member.

The pressure relief valve preferably yet further includes the aforementioned external cap having a cylindrical bore therein with the bore being adapted to slidably receive the internal member via an opening thereto and with the remaining end of the bore being closed, with the bore being of sufficient depth to receive the internal member when the cap is in facing engagement with the test head.

The pressure relief valve yet further includes an axially elongated intermediate member having a central preferably cylindrical passageway extending therethrough. The axially elongated intermediate member includes a central portion preferably having a hexagonal exterior with an annular shoulder preferably being formed about the passageway on one end of the central portion and having an axially facing annular surface preferably formed on the opposite end of the central portion. The intermediate portion further includes a first larger end portion of generally tubular configuration extending preferably coaxially with the central cylindrical bore and being externally threaded for mating engagement with the threaded passageway. The axially elongated intermediate member still further preferably includes a smaller second end portion of generally tubular configuration, extending coaxially with the central cylindrical bore and being externally threaded at the end thereof remote from the central portion. The external threads of the smaller second end portion of the intermediate member mesh with internal threads in a bore in the external cap, which is removable.

The pressure relief valve disclosed in parent application U.S. Ser. No. 13/222,290 is retrofitable to portable Brinell hardness testers of the type disclosed in the U.S. Pat. Nos. 3,192,582 and 4,361,034 as presently manufactured by King Tester Corporation, King of Prussia, Pa., and in many bolt-for-bolt copies of these testers as made by numerous copyists around the world, so long as the copy is of reasonable quality.

The pressure relief valve disclosed in parent application U.S. Ser. No. 13/222,290 when assembled has the recess of the interior member cylindrical first end fitting over and receiving the lesser diameter second portion of the cylindrically configured cap, with the bore of the interior member cylindrical first end portion preferably positioned to receive the shaft upon axial movement of the circular head and resultant compression of the spring. The external threads on the interior member first end are of the same diameter and pitch as those on the externally threaded surface of the larger first end of the intermediate member, with both sets of external threads being adapted to threadedly engage a passageway in which the valve is to be positioned.

The pressure relief valve disclosed in parent application U.S. Ser. No. 13/222,290 preferably further has an axially facing annular surface of the cylindrical first end of the interior member and an axially facing annular surface of the intermediate member first end that are in facing contact with one another. The elongated central cylindrical portion of the interior member extends slidably through the central cylindrical passageway of the intermediate member. The cylindrical second end of the interior member preferably extends slidably through and outwardly of the intermediate member, preferably providing access to the horizontal receptacle of the interior member first end. With this arrangement, upon manual hexagonal wrench rotation of the interior member, the interior member preferably moves axially within the threaded passageway due to threaded engagement thereof with the threaded passageway. The interior member cylindrical first end preferably moves the cap axially, with the valve stem exerting greater or lesser force at the valve seat according to the direction of axial movement of the interior member, thereby compressing or relieving the spring.

In yet another one of its aspects, parent application U.S. Ser. No. 13/222,290 provides a portable metal hardness tester with a test head preferably mounted in a carriage for applying preferably preselected force to a test piece. The force is preferably generated by application of manually-pumped hydraulic fluid into a ram pressure chamber preferably to move a ram cylinder within the test head towards the test piece, where the portable metal hardness tester preferably includes a pumping handle mounted on a rotatable shaft connected to the test head, and gears within the test head for converting rotary motion of the shaft, resulting from operator manual force applied to the pumping handle, into longitudinal movement of a hydraulic fluid pumping piston within the test head, with a stop preferably being connected to the carriage for limiting angular movement of the pumping handle turning the rotatable shaft.

The "stop" or stroke limiter structure of the portable Brinell metal hardness tester embodying the invention(s) of parent application U.S. Ser. No. 13/222,290 prevents breakage of the tester hydraulic pump gear and rack combination, which may otherwise result from overzealous use of the tester when overeager or undereducated operators inadvertently apply excessive of force to the pump handle. The stop or stroke limiter structure limits the length of the stroke of the pump handle, at the end of the stroke, in such a way as to prevent the pump handle from being overextended and perhaps breaking. The stroke limiter structure does not interfere with operation of the portable Brinell metal hardness tester. However, presence of the stop or stroke limiter structure may require the operator to make two or three additional strokes of the pump handle in order to reach and apply the maximum hydraulic load of 3,000 kg. of force. It does not affect lower loads such as 500 kg., 1,000 kg., and 1,500 kg.

The stroke limiter stop structure portion of the portable Brinell metal hardness tester manifesting aspects of the U.S. Ser. No. 13/222,290 invention may be removed, once the operator learns proper operation of the portable Brinell metal hardness tester. The stroke limiter structure may also be retrofitted to portable Brinell metal hardness testers of the type disclosed in U.S. Pat. Nos. 3,129,582 and 4,361,034.

In yet still another aspect, parent application U.S. Ser. No. 13/222,290 provides a portable Brinell metal hardness tester including a carriage moveable along vertically elongated elevating screws, a test head mounted in the carriage for applying preselected force to a test piece, where the test head includes a pressure release valve, with the pressure release valve including a shaft extending outwardly from the test head and an upstanding handle for actuation of the pressure release valve. The handle preferably includes a ring-like portion with a preferably internally fluted aperture formed therein for receiving and gripping the extending shaft portion of the pressure release valve.

The pressure release valve handle portion preferably has a planar lower surface for flush fitting with an exterior surface of the test head. The handle further preferably includes a blade-like extension portion configured for gripping between an operator's thumb and forefinger, with the extension portion extending vertically away from the preferably planar lower surface of the handle a distance greater than the ring-like portion. The extension portion preferably further includes a first vertically extending edge extending proximate the ring-like portion and a second vertically extending edge preferably at an extremity remote from the ring-like portion, with the second vertically extending edge preferably being longer than the first vertically extending edge, and with extremities of the first and second vertically extending edges remote from the planar surface preferably being connected by a straight edge.

In yet another one of its aspects parent application U.S. Ser. No. 13/222,290 provides a tampering detector for use with a portable Brinell hardness tester having a test head for applying preselected force to a test piece, by manual pumping of hydraulic fluid to apply hydraulic fluid pressure of a preselected level to a ball contacting a test piece, where the test head includes an adjustable pressure relief valve, preferably of the type described above, for relieving hydraulic fluid pressure at an adjustably selected level. The adjustable pressure relief valve has a preferably external cylindrical cap portion at one extremity with the external cylindrical cap having a threaded bore for the connection with an intermediate portion of the pressure relief valve extending from the test head. The cylindrical cap is preferably exterior of the test head.

The tampering detector preferably comprises a laminar sheet preferably having a first portion with a preferably circular periphery for fitting on a circular top of the valve cylindrical cap, a second portion having preferably parallel sides and extending radially away from the first portion, and a third portion connected to the second portion remotely from the first portion, having preferably parallel sides that are preferably perpendicular to the sides of the second portion. Adhesive preferably secures the sheet first portion to the cylindrical cover and the sheet third portion to the valve intermediate portion extending from the test head, so that the frangible sheet must be torn when separating the valve cap from the valve intermediate portion, thereby indicating tampering with the pressure relief valve. In one embodiment disclosed in parent application U.S. Ser. No. 13/222,290 the sheet is preferably paper. In another embodiment disclosed in parent application U.S. Ser. No. 13/222,290 the sheet is preferably polymeric. The sheet desirably accepts ink. Also desirably, the circular periphery of the first portion is of lesser diameter than the cylindrical cover.

In one of its aspects, this invention provides a portable Brinell metal hardness tester having a test head mounted in a movable carriage riding elevating screws for applying pre-selected force to a test piece by manual pumping to apply hydraulic pressure to a ball contacting the test piece in accordance with the Brinell method of testing. The tester in its preferred manifestation desirably includes a reciprocable pumping rack movable in response to movement of a pumping lever for pumping hydraulic fluid into a passageway at test head to increase hydraulic fluid pressure in the test head to a level required for metal hardness testing. The tester further includes in its most desirable manifestation a stent located in the passageway for pumped hydraulic fluid flow through the passageway into the test head of the tester to apply hydraulic fluid to the ball with its stent contacting and interferingly stopping the rack upon movement of the rack into the passageway by a pre-selected amount. The rack is desirably movable perpendicularly to the passageway. Most desirably, the rack is movable vertically and the passageway is horizontal.

The stent is desirably tubular and is further desirably co-axial with the passageway. The stent further desirably has a slot formed in one end and has a lateral depression intersecting the stent interior with the depression being hemispherical. Most desirably, the depression is aligned with the rack when the tester is assembled.

In another one of its aspects, this invention provides a portable Brinell metal hardness tester having a pumping rack movable in a fluid duct extending through a test head of the tester. The rack is provided for pumping hydraulic fluid from the duct into a passageway with which the duct communicates in the test head, thereby to increase hydraulic fluid pressure in the test head to a level required for metal hardness testing. In this manifestation of the invention, the tester desirably further includes a member positioned in the duct that the end thereof communicating with the passageway, the member halting movement of the pumping rack along the duct towards the passageway upon contact therewith.

The member is desirably tubular, with the tubular member exterior facingly contacting the wall of the duct. The member desirably has open ends.

The tester desirably further includes a check valve residing in the passageway at juncture with the duct, with the tubular member extending within the duct into the passageway and with the tubular member having a recess formed therein receiving the check valve. Most desirably, the recess is a lateral recess. Further desirably, the duct and the passageway are preferably perpendicular to one another.

The rack is preferably movable vertically and the passageway is preferably horizontal. The tubular member is preferably co-axial with the passageway and has a slot in one end. The tubular member further desirably has a lateral depression intersecting an open interior of the tubular member where the depression is hemispherical and is aligned with the rack.

In still another one of its aspects, this invention provides a portable Brinell metal hardness tester having a test head mounted in a movable carriage for applying pre-selected force to a test piece by pumping hydraulic fluid pressure to a ball contacting the test piece and includes a rack movable within a passageway in response to movement of a lever for pumping hydraulic fluid into a passageway of the tester to increase hydraulic fluid pressure to a level required for metal hardness testing, and further includes a blocking member in the form of a stent for permitting pumped hydraulic fluid to flow through the passageway into the test head to apply hydraulic fluid to the ball contacting a test piece while interferingly stopping the rack upon movement of the rack by a pre-selected amount.

The rack is preferably movable perpendicularly to a horizontal passageway, and most preferably the rack is movable vertically in a vertical passageway and the passageway for pumped hydraulic fluid flow is horizontal. Preferably, the stent is tubular and coaxial with and dispersed largely within a vertical passageway.

BRIEF DESCRIPTION OF THE DRAWINGS

In the drawings, the "front" is considered to be the portion of the tester facing the viewer in FIG. 1, which is the portion of tester to the viewer's left in FIG. 2. Hence, the side of the tester facing the viewer in FIG. 2 is considered to be the "right" side of the tester, since that is the side of the tester that is to the viewer's right in FIG. 1.

DESCRIPTION OF THE PREFERRED EMBODIMENTS AND BEST MODE KNOWN FOR PRACTICE OF THE INVENTION

Figure 1:
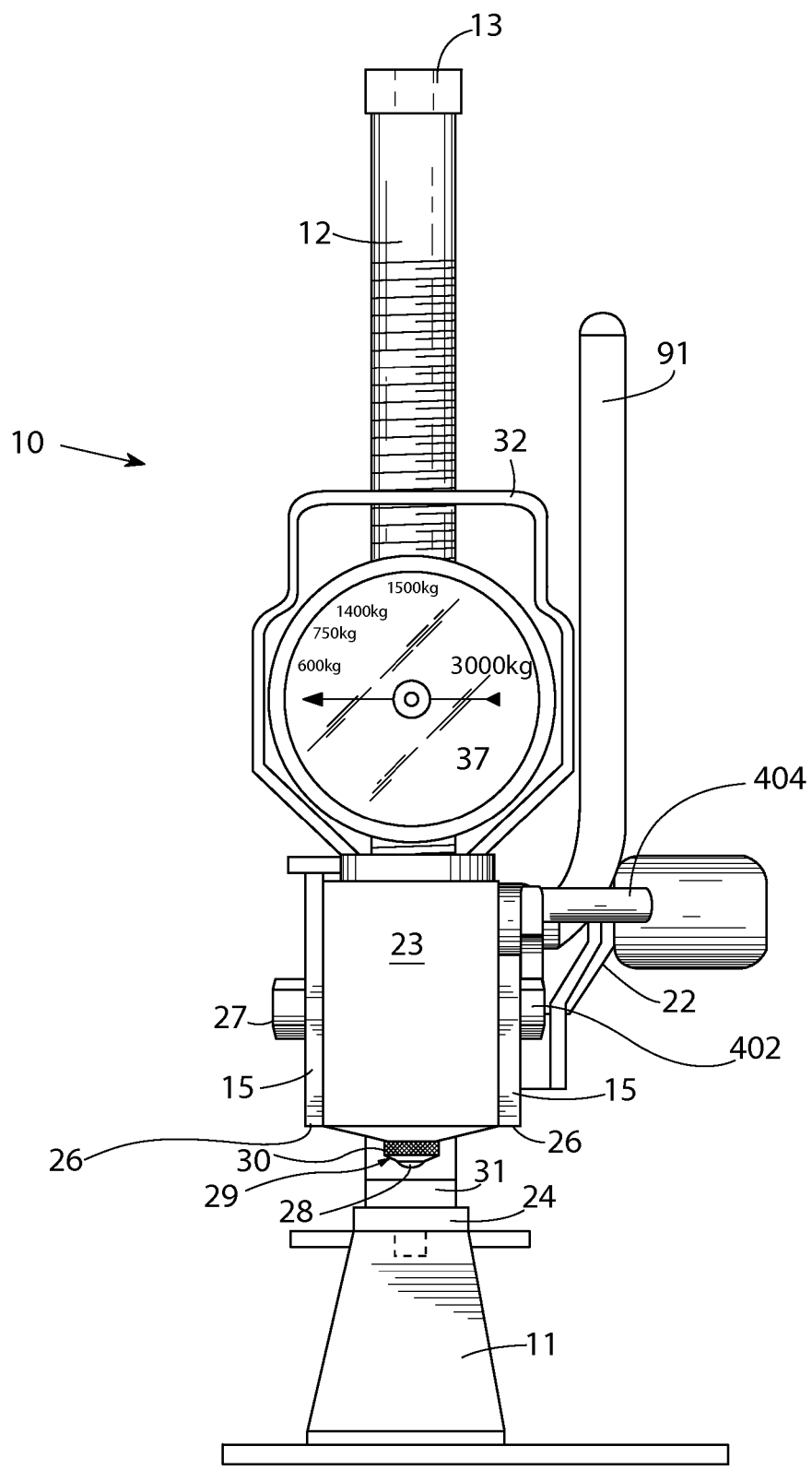
FIG. 1 is a front elevation of a portable Brinell metal hardness tester manifesting aspects of the invention.
Figure 2:
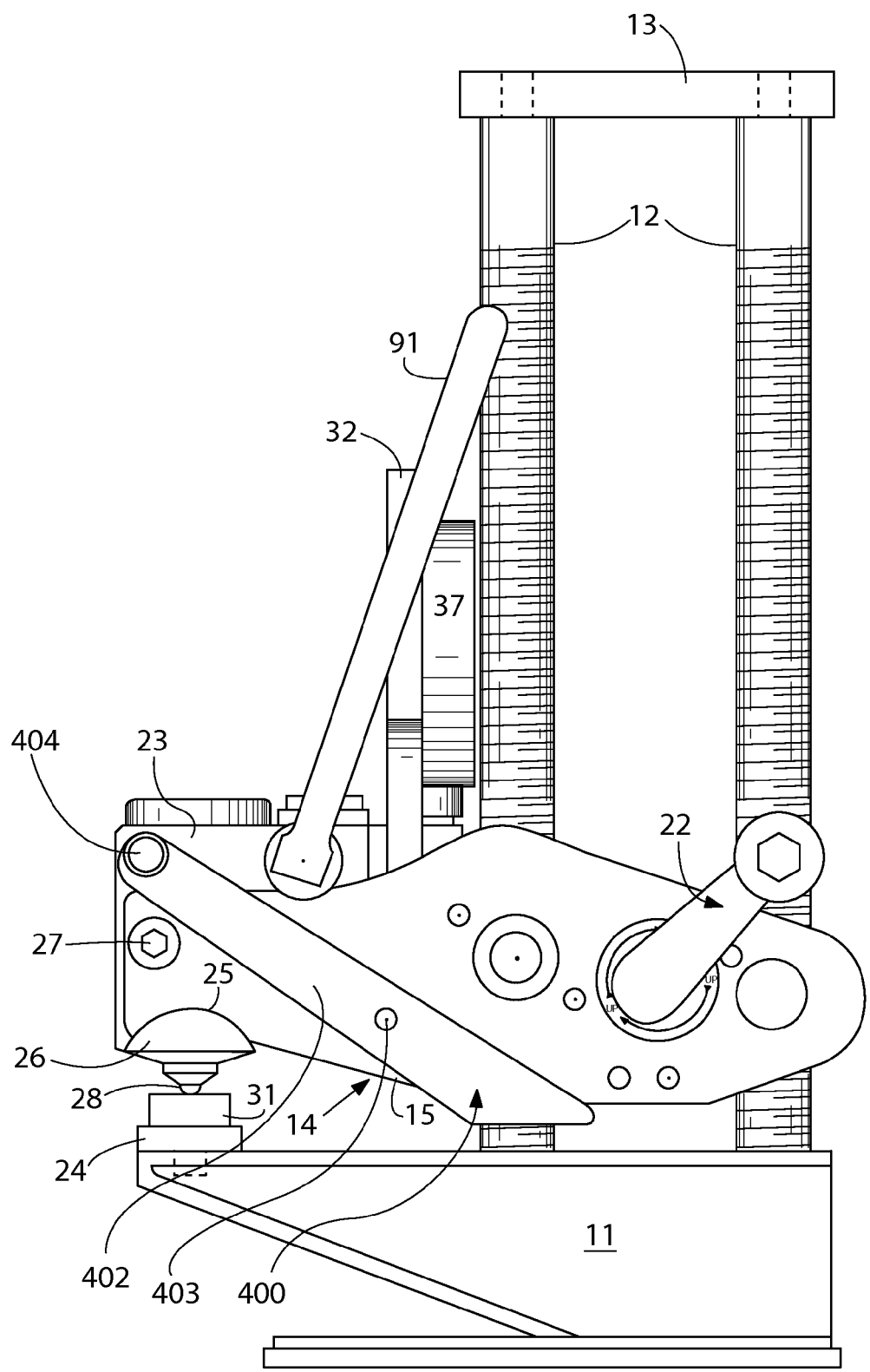
FIG. 2 is a right side elevation of the portable Brinell metal hardness tester illustrated in FIG. 1, with a pumping lever shown spaced from the a pump stroke limiter.

Referring generally to FIGS. 1 through 4 and of the drawings, and particularly to FIGS. 1 and 2, a portable Brinell metal hardness tester designated generally 10 includes a base 11 supporting a pair of upstanding elevating screws 12, which are preferably connected together at the top by a horizontal strap 13. Strap 13 helps maintain screws 12 parallel and also provides a handle by which the portable Brinell metal hardness tester may be carried.

A carriage designated generally 14 is mounted for preferably vertical movement along the two elevating screws 12. Carriage 14 includes two parallel side plates 15 preferably connected together by blocks 16, shown best in FIG. 4, held in place by suitable bolts not numbered in the drawings, which rotatably support ring gears 17, the internal teeth of which mesh with elevating screws 12.

The external teeth of ring gears 17 are driven by a gear 18, rotating about a vertical axis. Gear 18 meshes with a gear 21 rotatably mounted on side plate 15. Gear 21 is driven by a hand crank assembly 22. Upon manually turning a handle portion 22A of hand crank assembly 22 and thereby rotating the crank 22B of hand crank assembly 22, gear 21 turns unitarily with crank 22B and drives gear 18 which in turn causes ring gears 17 to rotate. As the internal teeth of rotating ring gears 17 engage the external threads of elevating screws 12, carriage 14 may be raised or lowered as desired.

Figure 4:
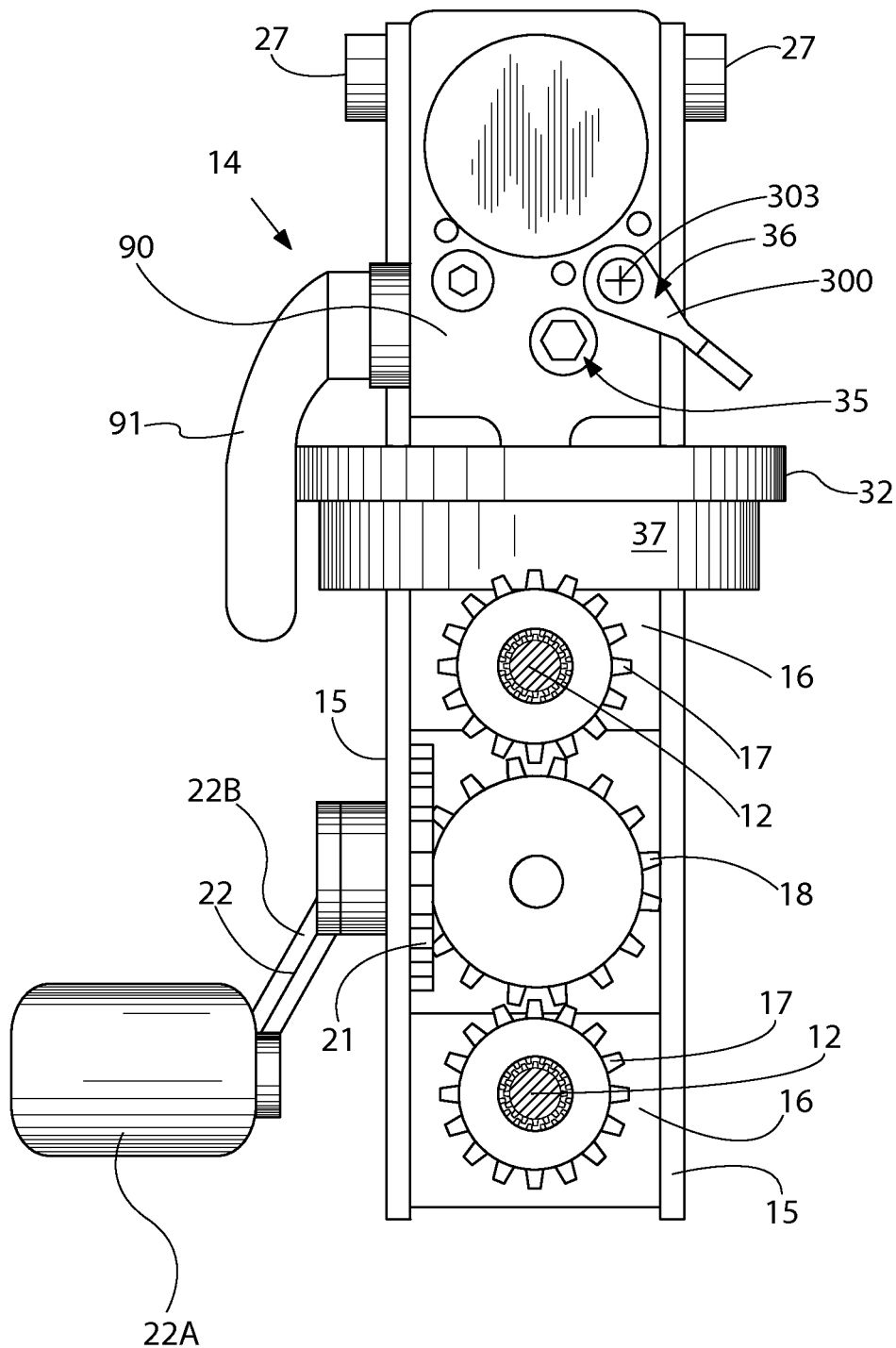
FIG. 4 is a top plan view, in somewhat schematic form, of the portable Brinell metal hardness tester illustrated in FIGS. 1 through 3, with the carrying handle removed and the elevating screws depicted in section.

As best shown in FIGS. 2 and 4, the front ends of side plates 15 are spaced apart and receive a test head designated generally 23, which is maintained in a predetermined position by side plate 15 over an anvil 24. Anvil 24 is supported on base 11. Downwardly facing arc-shaped surfaces 25 formed in side plates 15 engage correspondingly shaped arc-shaped ears 26 extending from the sides of test head 23 as best shown in FIG. 2, thereby maintaining test head 23 in position respecting anvil 24. Screws 27 hold side plates 15 against test head 23. The bottom extremities of arc-shaped ears 26 are visible in FIG. 1.

Referring to FIG. 2, the arcs defining arc-shaped surfaces 25 and corresponding arc-shaped surfaces of ears 26 are struck from an axis which includes, and moves from, the center of a ball 28, which in turn is carried by test head 23. The axis extends normal to the conventional, usual vertical path of movement of ball 28, whereby forces acting through arc-shaped surfaces 25, when the tester is in use, are substantially radial with respect to ball 28. As a result, lateral thrust due to off-center application of force to ball 28 and consequent inaccurate test readings are minimized.

When a test piece, such as that shown as 31, is placed between ball 28 and anvil 24 as illustrated in FIGS. 1 and 2, portable Brinell metal hardness tester 10 may be operated to determine the Brinell hardness of the test piece 31. Ball 28 is preferably mounted in and held in place by a holder 29 having a knurled external surface portion 30. Holder 29 is desirably internally threaded for engagement with a threaded extension portion of ram 55, not shown in the drawings, as being in internal engagement with holder 29.

Test head 23 may be removed from carriage 14 by loosening screws 27 and lifting head 23 from between side plates 15 using handle 32.

Figure 5:
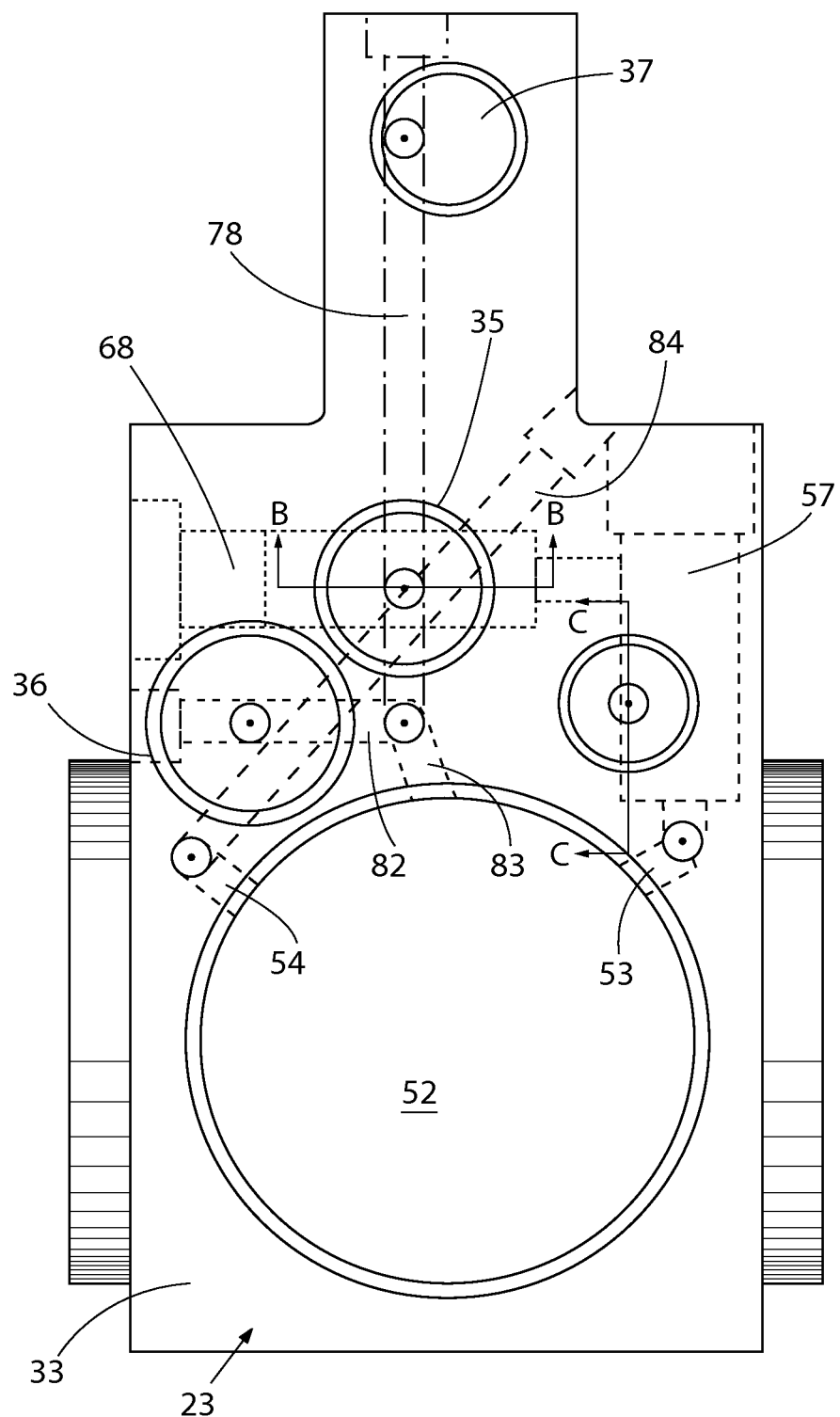
FIG. 5 is a top plan view of a test head portion of the portable Brinell metal hardness tester illustrated in FIGS. 1 through 4.

Referring principally to FIGS. 5, 6, 7, 9, 10, 11, 12, and 13, test head 23 includes a preferably unitary test block 33 that has a manually powered pump designated generally 34 and shown somewhat schematically in FIGS. 6, 9, 19, and 11, a pressure relief valve designated generally 35, and a pressure release valve designated generally 36, both of which are shown schematically in the FIG. 5 top view. A gauge 37, shown in FIG. 1, is mounted on test block 33 and indicates the hydraulic pressure being applied to ball 28 as ball 28 contacts and indents a test piece 31.

Test block 33 of test head 23 has formed therein a ram cylinder 38, which is preferably high strength steel and has a cup-like configuration, and a pump cylinder 41, which is in the form of a tubular passageway extending vertically within test block 33. Both ram cylinder 38 and pump cylinder 41 are illustrated in FIGS. 6, 9, 10, and 11. Test block 33 further includes a pressure relief valve chamber 42, a part of which is the bottom portion of pump cylinder 41 below pump plunger 94 shown in FIG. 6. Pressure relief valve chamber 42 is shown in dotted lines in FIG. 12. Test block 33 further includes a pressure release valve chamber 43 shown in dotted lines in FIG. 13.

An oil sump 44, which is shown in FIGS. 6, 9, 10, and 11 and may contain any suitable hydraulic fluid, is provided by a cuplike casing 45, which is desirably high strength steel and which fits within ram cylinder 38. The upper part of casing 45 has a flange 46 that is press-fitted to make oil-tight contact with the walls of ram cylinder 38. The lower part of casing 45 is spaced inwardly from ram cylinder 38 to leave an annular space defining a ram pressure chamber 56.

Figure 6:
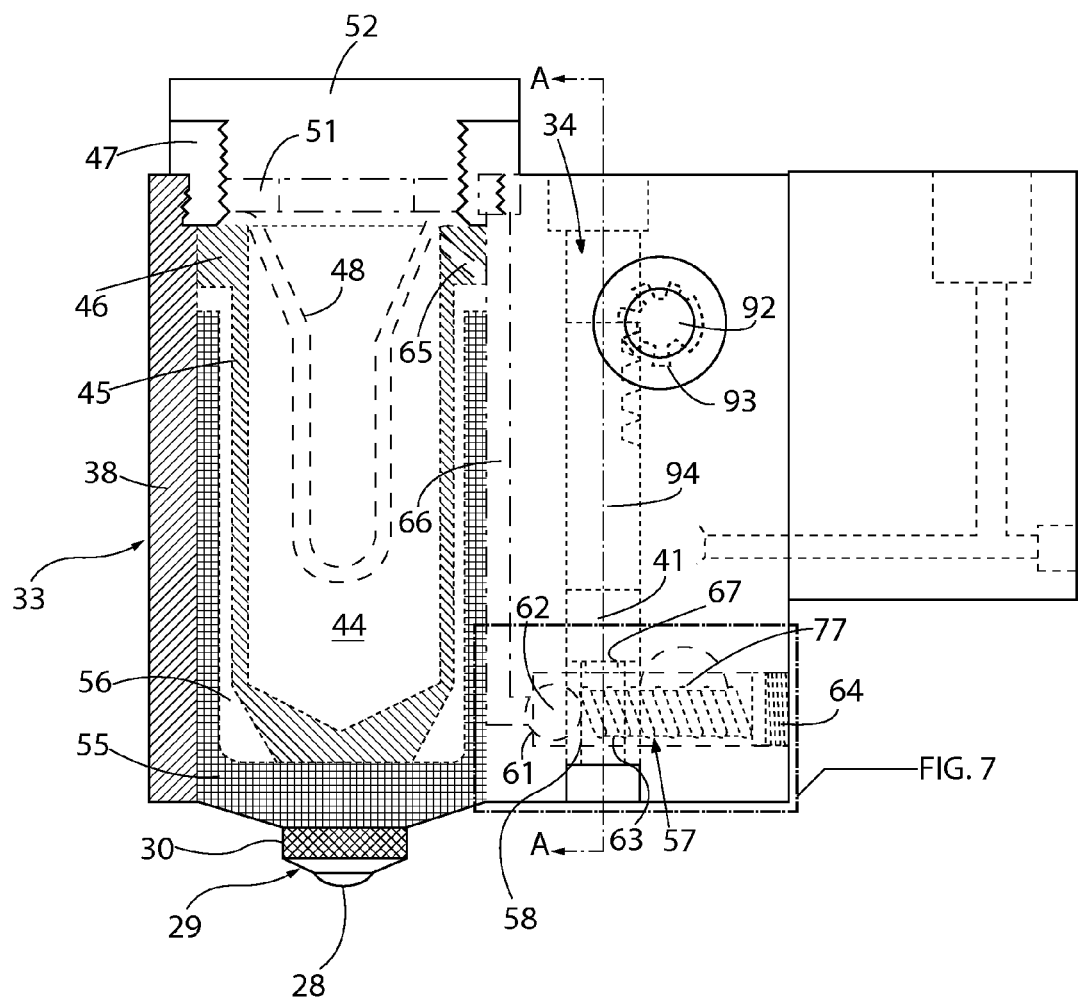
FIG. 6 is a right side elevation of the test head illustrated in FIG. 5.

As shown in FIGS. 6, 9, 10, and 11, the upper end of ram cylinder 38 is threaded to receive a retaining nut 47, which bears downwardly against the upper surface of flange 46 to lock casing 45 in place. A flexible, hydraulic fluid-impermeable sack 48 is positioned in oil sump 44. Sack 48 is preferably held in place by downward force exerted by a threaded washer 51, which preferably engages threads on the inner wall of retaining nut 47. Sack 48 prevents oil from escaping from sump 44 and expands and contracts under varying oil pressure conditions within sump 44. A cap 52 is threaded on to retaining nut 51, as illustrated in FIG. 6.

Cup-like casing 45 has only one exit port 53, shown in FIG. 5, leading away from sump 44, and has only one return port 54, also shown in FIG. 5, leading back into sump 44. Ports 53 and 54 illustrated in FIG. 5 to be spaced apart by about 95° in casing 45 in order to inhibit leakage therebetween.

As shown in FIGS. 6, 9, 10, and 11, a cuplike ram 55 is positioned in ram cylinder 38 and has a ram pressure chamber 56 formed between the annular interior surface of ram 55 and the exterior of oil sump casing 45.

Figure 7:
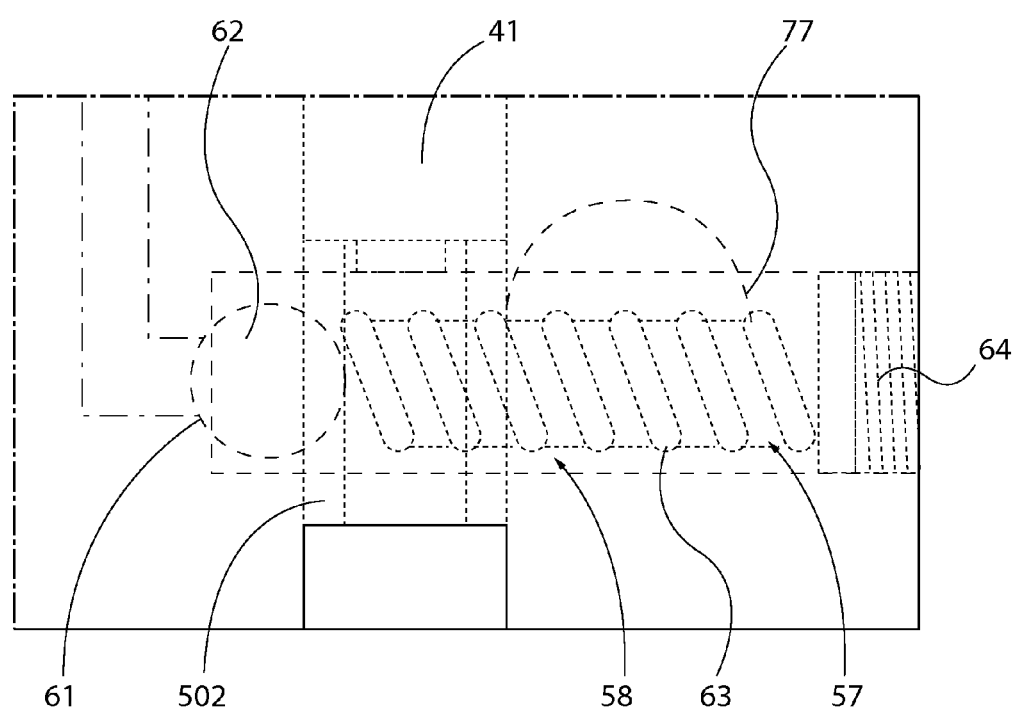
FIG. 7 is an enlarged view of the structure within the dotted line labeled "FIG. 7" in FIG. 6.

A low pressure check valve designated generally 57 and illustrated in FIGS. 6, 7, 9, 10, and 11, with the best illustration being in enlarged FIG. 7, resides in a longitudinally elongated low pressure valve chamber 58 formed in test block 33. Check valve 57 controls a supply port 61 providing entrance into the generally higher oil pressure region of the test head 23, to the left considering FIGS. 6, 7, 9, 10, and 11, with a ball check 62 being urged toward supply port 61 to define the closed position of supply port 61 by a first end of a preferably coil spring 63, which has a remaining end abutting a screw 64 threaded into the outer wall of test block 33 and defining a closed end of longitudinally elongated low pressure valve chamber 58. Exit port 53, illustrated and numbered in FIG. 5, of sump 44 is connected to supply port 61, which is controlled by low pressure check valve 57, by a passageway which includes an angular duct 65 and a vertical duct 66, both of which are illustrated and numbered in FIG. 6.

Longitudinally elongated low pressure valve chamber 58, within which low pressure check valve 57 resides, communicates directly with a pumping cylinder 41 via a vertical duct 67 as shown in FIG. 6.

Figure 12:
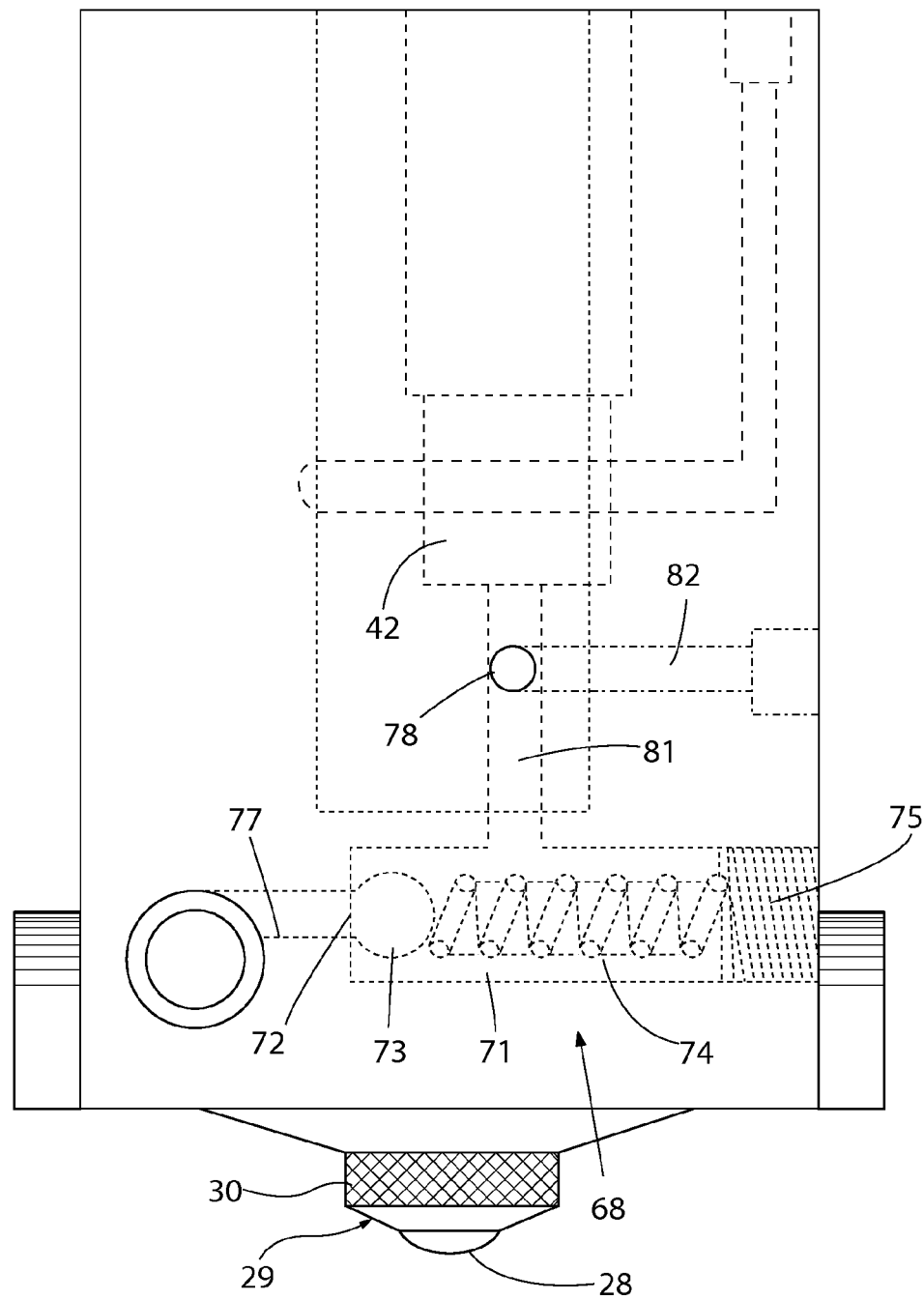
FIG. 12 is a rear elevation of the test head illustrated in FIGS. 5 through 11.

Referring to FIG. 12, a high pressure valve designated generally 68 resides in a chamber 71 formed in test block 33 and that includes an entrance port 72. A ball check valve 73 resides in entrance port 72 and is urged towards the closed position by a first end of a preferable coil spring 74 having its remaining end abutting a closure screw 75, which is threaded into the outside wall of test block 33, all as shown in FIG. 12.

Still referring to FIG. 12, a passageway including duct 77 connects low pressure valve chamber 58 (shown and numbered in FIGS. 6, 7, 9, 10, and 11) to the entrance port 72 of high pressure valve 68, whereby oil may be pumped from pumping cylinder 41 (shown in FIGS. 6, 9, 10, and 11) into low pressure valve chamber 58 (shown and numbered in FIGS. 6, 7, 9, 10, and 11) and from there through duct 77 to a high pressure valve designated generally 68 in FIG. 12.

The axis of the high pressure valve 68 is turned ninety degrees (90°) from the axis of low pressure valve 57 as is apparent when comparing FIG. 12 to FIGS. 6, 9, 10, and 11.

The passageway leading from high pressure valve chamber 71 to gauge 37 includes a duct 78, shown in FIGS. 5 and 12, that is horizontally positioned, is ninety degrees (90°) from the axis of high pressure valve chamber 71, and is parallel to the axis of low pressure valve chamber 58. This facilitates drilling of the valve chambers and ducts in the course of manufacture of test block 33, since all except one of the chambers, passageways, and ducts are normal to the surface of the outside wall of test block 33 into which they are drilled when test block 33 is fabricated.

Figure 15:
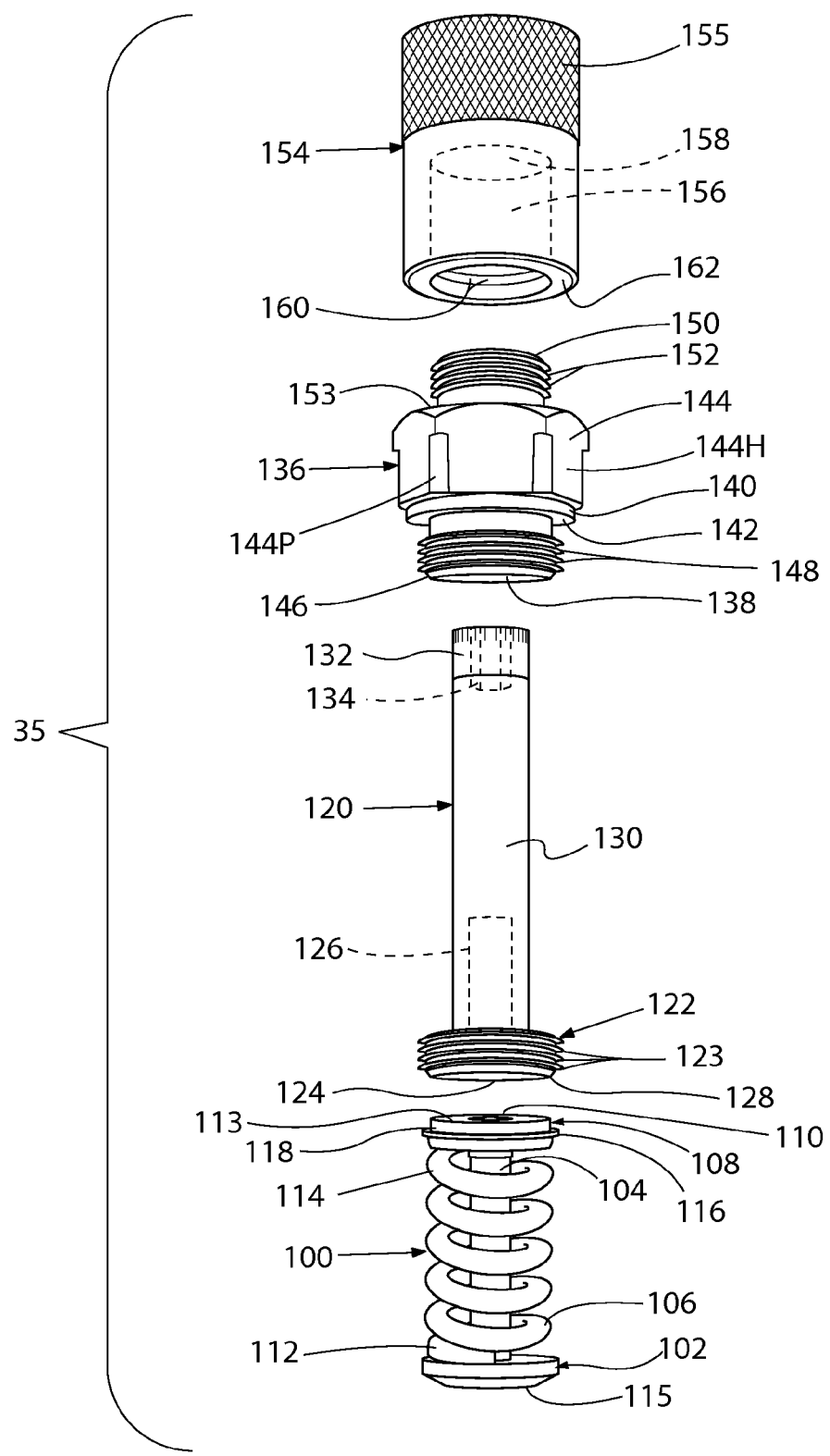
FIG. 15 is an exploded view of a adjustable pressure relief valve manifesting aspects of the invention, with views of some of the components taken looking slightly upwardly or downwardly, to provide depth to the drawing and thereby to enhance drawing clarity and ease of understanding.
Figure 16:
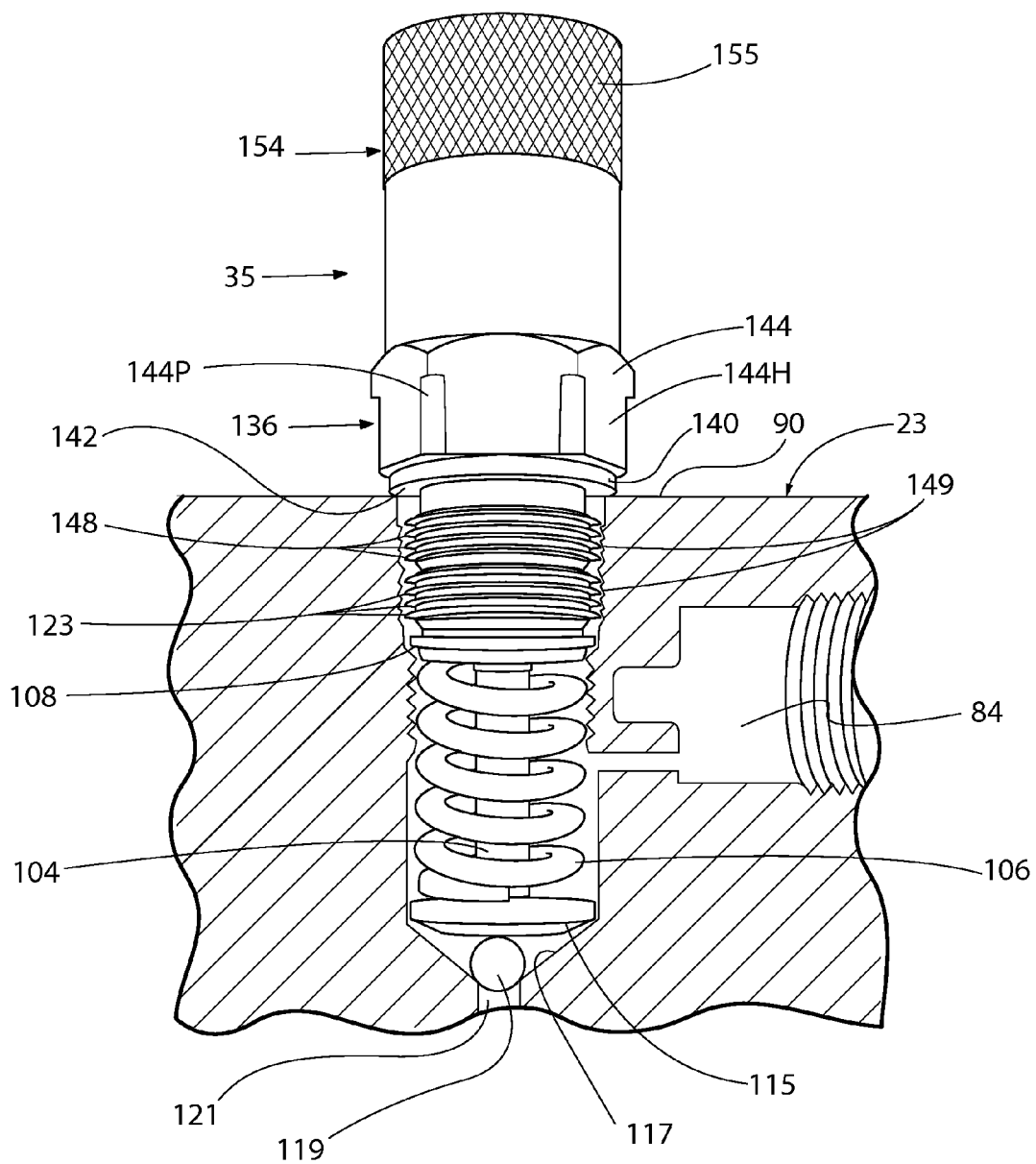
FIG. 16 is a sectional view taken at lines and arrows B-B in FIG. 5 of the adjustable pressure relief valve, shown in FIG. 15, assembled in place within the test head portion of the portable Brinell metal hardness tester illustrated in FIGS. 1 through 4 and 14, with views of some of the components taken looking slightly upwardly or downwardly, to provide depth to the drawing and thereby to enhance drawing clarity and ease of understanding.

As illustrated in FIG. 12, high pressure valve chamber 71 is connected to pressure relief valve 35 (which is positioned in pressure relief valve chamber 42 and is schematically illustrated in FIG. 5 and illustrated in detail in FIGS. 15 and 16) through a passageway including a vertical duct 81. High pressure valve chamber 71 is also connected to pressure release valve 36 (which is illustrated schematically in FIG. 5 and is shown in more detail in FIGS. 19 and 20) by a passageway including horizontal duct 82 shown in FIG. 5. High pressure valve chamber 71 is yet further connected to gauge 37 through a passageway including horizontal duct 78 shown in FIG. 12. Finally, high pressure valve chamber 72 is also connected to ram pressure chamber 56 through a passageway including a horizontal duct 82, illustrated and numbered in FIGS. 5 and 12.

Figure 13:
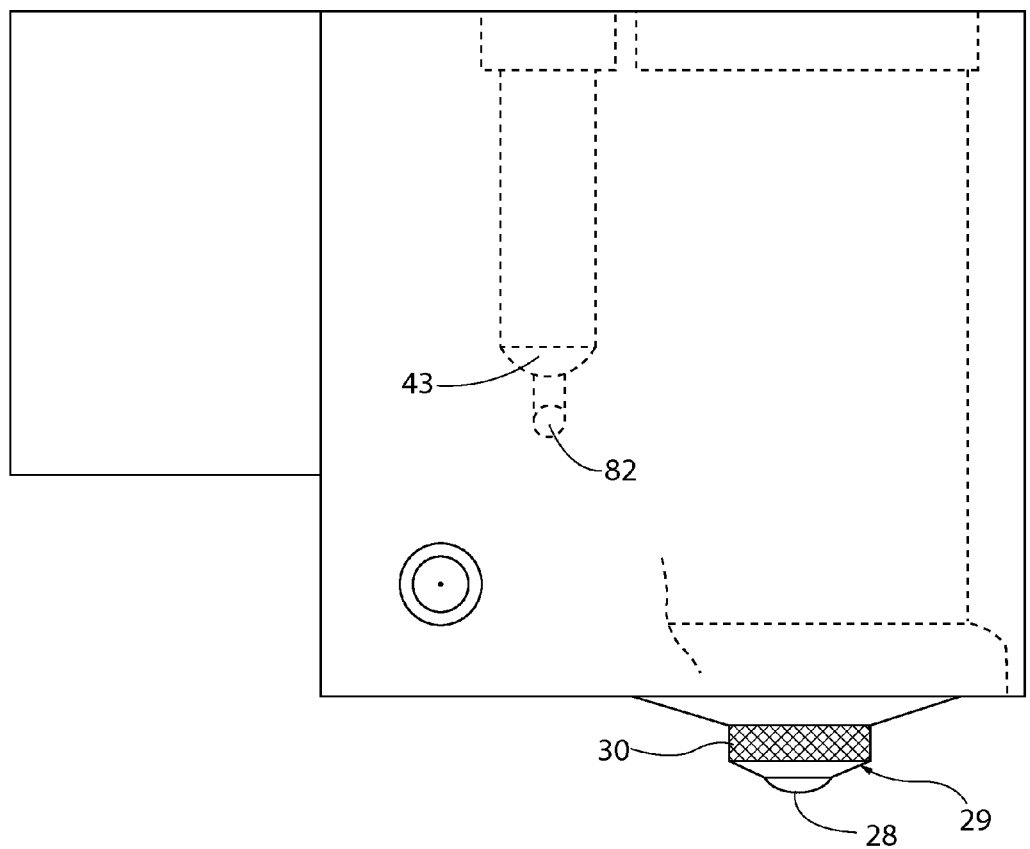
FIG. 13 is a left side elevation of the test head illustrated in FIGS. 5 through 12.

A return passageway including a diagonal duct 84, illustrated and numbered in FIG. 5, connects the pressure relief valve chamber 42, illustrated in FIG. 12, and the pressure release valve chamber 43, illustrated in FIG. 13, to oil sump 44 illustrated in FIG. 5 through return port 54 also illustrated in FIG. 5. During normal operation, the portion of diagonal duct 84 extending to the upper right from pressure relief valve 35 in FIG. 5 is plugged. The diagonal positioning of diagonal duct 84 is necessitated by the drilling sequence during manufacture of test block 33.

Pump 34, which is shown generally in FIGS. 6, 9, 10, and 11 includes a pump handle 91 (illustrated in FIGS. 1 through 4) attached to a shaft 92 to which is keyed a segmented gear 93, as shown in FIGS. 6, 9, 10, and 11. Segmented gear 93, shown in dotted lines in FIGS. 6, 9, 10, and 11, meshes with rack teeth 500, (shown in dotted lines in FIGS. 6, 9, and 11 and in solid lines in FIG. 10) formed in a vertically reciprocable pumping plunger 94, which is also shown in dotted lines in FIGS. 6, 9 and 11 and in solid lines in FIG. 10.

Manual up and down pumping motion applied to pump handle 91 results in rotation of segmented gear 93. As segmented gear 93 rotates, engagement of the teeth of segmented gear 93 with rack teeth 500 of pumping plunger 94 results in movement of pumping plunger 94 up and down, pumping oil from within pump cylinder 41, through duct 67, and into low pressure valve chamber 58, all in response to manual reciprocating arcuate movement of pump handle 91.

When pumping plunger 94 is raised, the resulting low pressure in pump cylinder 41 draws oil from sump 44 through exit port 53 (both shown in FIG. 5), duct 65 and vertical duct 66 (both shown in FIGS. 6, 9, 10, and 11) into low pressure valve chamber 58, past ball check 62, and through duct 67 into pump cylinder 41, as is apparent from FIGS. 6, 9, 10, and 11.

Then, as pumping plunger 94 is moved downwardly by corresponding movement of pump handle 91, rotating shaft 92 and segmented gear 93, segmented gear 93 engages rack teeth 500 of pumping plunger 94 moving pumping plunger 94 downwards in FIGS. 6, 9, 10, and 11, and oil trapped within pumping cylinder 41 is forced under pressure into low pressure valve chamber 58. Since ball check valve 62 is seated by the force exerted by spring 63 and the pressure of the oil from pumping cylinder 41, oil is forced under pressure through duct 77 (shown in FIG. 7 in detail and also shown in FIGS. 6, 9, 10, and 11) to entrance port 72 of high pressure valve 68 (both shown in FIG. 7) where the pressure of the oil forces the oil past ball check valve 73 and into high pressure chamber 71.

Oil reaching high pressure chamber 71 cannot reverse its direction of flow due to the presence of ball 73, which seats due to the action of spring 74 when the pressure of the oil from duct 77 diminishes. As pumping continues, oil flows from high pressure chamber 71 through vertical duct 81 shown in FIG. 12 and horizontal duct 83 shown in FIG. 5, into ram pressure chamber 56 shown in FIG. 6. As more oil is forced into pressure chamber 56, pressure gradually builds therein to move hydraulic ram 55.

Ram pressure chamber 56 communicates with pressure gauge 37, pressure release valve 36, and pressure relief valve 35, so that oil pressure thereamong is uniform.

Pressure relief valve 35, described in more detail below, is manually preset to open at a selected oil pressure.

Referring to the structure illustrated in FIGS. 15 and 16, when oil pressure is too high, oil pressure forces the circular head 102 of valve stem 100 of pressure relief valve 35 away from its seat and oil flows through the pressure relief valve chamber 42 depicted in FIG. 12, emptying into sump 44 through diagonal duct 84 and return port 54. Diagonal duct 84 and return port 54 are illustrated in FIG. 5.

Figure 14:
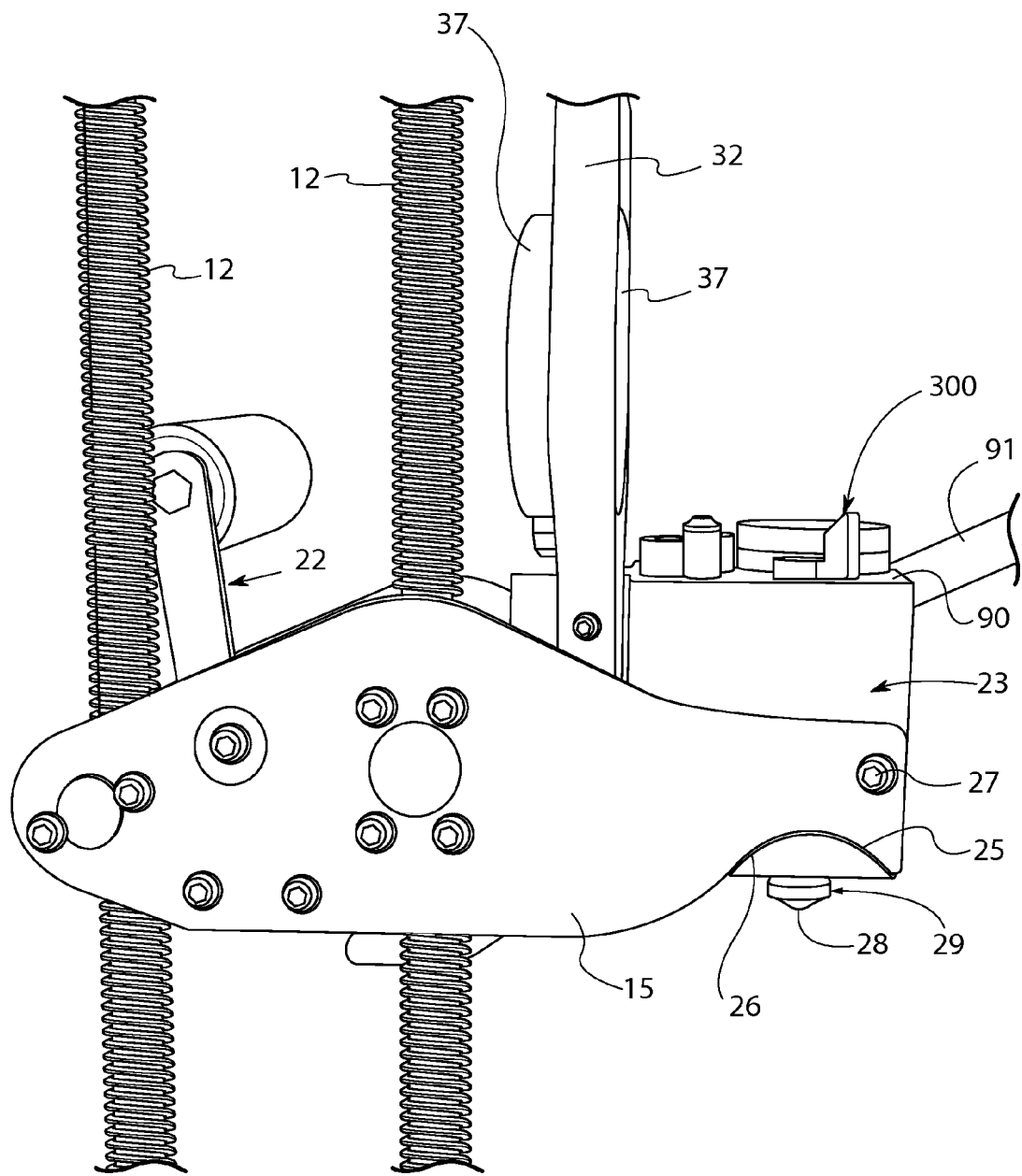
FIG. 14 is a broken left side elevation of the portable Brinell metal hardness tester illustrated in FIGS. 1 through 4, with the view taken from slightly right of center, to enhance drawing clarity and ease of understanding, with the pressure release valve handle 300 being particularly well shown.

Pressure release valve 36 is manually operated by turning handle 300 illustrated in FIG. 14, which allows oil in high pressure duct 82 to flow through pressure release valve chamber 43 shown in FIG. 13, and from there through diagonal duct 84 to return to sump 44 via return port 54 as shown in FIG. 5.

Operation commences with pressure release valve 36 being opened by manually turning handle 300. Carriage 14 is raised enough to admit a test piece 31 into the space between anvil 24 and ball 28. Test piece 31 is then firmly clamped between ball 28 and anvil 24, making sure that ram 55 is pushed in (upwards in FIGS. 6, 9, 10, and 11) as far as possible. Pressure release valve 36 is closed by manual movement of pressure release valve handle 300.

Pump handle 91 is then slowly manually reciprocated until the preselected full pressure, as shown on gauge 37, causes pressure relief valve 35 to "pop off" three or four times, assuring that the oil in ram pressure chamber 56 is at the preselected pressure at which pressure relief valve 35 has been set to relieve or "pop off". With high pressure oil in ram pressure chamber 56 pressing against ram 55, ram 55 urges ball 28 against test piece 31, creating a spherical indentation/impression that when measured in conjunction with the known hydraulic pressure (as controlled by the oil pressure setting at which pressure relief valve 35 has been set to "pop off" and displayed on gauge 37), all in accordance with known Brinell test procedure, yields the Brinell hardness of the test piece, since the oil pressure is known and the dimensions of the tester are known, force exerted on ball 28 is easily calculated. Pressure release valve 36 is then manually opened, oil pressure drops and carriage 14 is raised. The impression made by ball 28 on test piece 31 is a standard Brinell impression and is read in the known manner.

As best illustrated in FIG. 2, base 11 is made with a narrow, shallow nose supporting anvil 24. This nose portion of base 11, extending beyond the front end of the bottom plate of base 11, allows tests to be made in small places, such as in tubes and the like. This gives tester 10 unlimited possibilities for quickly making tests in places and on parts that otherwise would be too cumbersome or be impossible to test. The tester can be operated in many positions, even upside down, and still make accurate tests.

For applying lesser loads, i.e. loads less than the maximum setting of pressure relief valve 35, the procedure is to manually move pump handle 91 to increase hydraulic pressure to achieve the desired load, as indicated on the dial of gauge 37. The pressure is held for a few seconds, if necessary, and is then released. Such tests are accurate, even if pressure relief valve 35 is not set to pop off automatically at these reduced loads.

For testing parts larger than those that will fit between anvil 24 and ball 28 when using base 11 and carriage 14, test head 23 may be removed from carriage 14 by removing screws 27. Parts of any size may then be tested by providing means, such as c-clamps and yokes, placed against cap 52 to take the thrust of the load.

Pressure relief valve 35 is illustrated in greater detail in FIGS. 15 and 16, being particularly well shown in exploded form in FIG. 15. Pressure relief valve 35 includes a valve stem assembly designated generally 100, with valve stem assembly 100 including a circular head 102, fixed to and located at one end of valve stem 100. A shaft 104 is fixedly connected to and extends upwardly from circular head 102 into a central passageway 110 formed in cylindrical cap 108 of valve stem assembly 100, with shaft 104 residing slidably in central passageway 110. A coil spring 106 is positioned between circular head 102 of valve stem 100 and cylindrical cap 108 of valve stem assembly 100, with a first end 112 of spring 106 riding on an annular planar upwardly facing surface 113 of circular head 102 of valve stem assembly 100. The second end 114 of spring 106 rests against a downwardly facing unnumbered annular surface of cylindrical cap 108, outboard of central passageway 110. Cylindrical cap 108 includes an annular outwardly facing surface 118, which defines a lesser diameter portion of cap 108.

Circular head 102 of valve stem 100 further includes a downwardly facing (as respecting FIG. 15 and the position and orientation of pressure relief valve 35 depicted therein), generally rounded surface 115 configured for tight mating against preferably conical valve seat 117 formed in test head 23, as illustrated in FIG. 16. Optionally, a ball 119 operating as a ball check, may be provided, as illustrated in FIG. 16, for rounded surface 115 to bear against, thereby forcing ball 119 against an opening 121 which would otherwise be at the vertex of valve seat 117, as illustrated in FIG. 16. Opening 121 communicates with high pressure valve chamber 71.

Pressure relief valve 35 further includes an interior member designated generally 120 in FIG. 15 with interior member 120 having a generally cylindrical first end 122, with a circular recess 124 formed in first end 122 of interior member 120. An axial bore 126 formed in recess 124 is coaxial with generally cylindrical first end 122 of interior member 120 and with interior member 120 in general. Axial bore 126 is sufficiently deep and is of slightly greater diameter than shaft 104 so that upon compression of spring 106, shaft 104 may extend slidably through the entirety of central passageway 110 in cylindrical cap 108 and slidably occupy at least a portion of axial bore 126 in interior member 120.

Generally cylindrical first end 122 of interior member 120 includes an annular surface 128 formed on first end 122 and facing oppositely and radially outwardly respecting recess 124.

Interior member 120 further includes an elongated central cylindrical portion 130 and a cylindrical second end 132 in which a hexagonal receptacle 134, not visible when the structure is drawn in the manner depicted in FIG. 15 and accordingly shown in dotted lines, is formed.

Still referring to FIG. 15, pressure relief valve 35 further includes an intermediate member designated generally 136, having an axial central passageway 138 extending therethrough, with the opening to passageway 138 being visible at the bottom end of passageway 138 in FIG. 15. Intermediate member 136 further includes an annular shoulder 140 formed on one surface of a generally hexagonally configured central portion 144 of intermediate member 136. Hexagonal central portion 144 preferably has six outwardly facing planar surfaces 144H, which give central portion its hexagonal configuration. Intermediate surfaces 144P are planar surfaces formed on central portion 144 of intermediate member 136, between the larger six outwardly facing flat hexagonal panel surfaces 144H that provide the generally hexagonal shape to hexagonal central portion 144 of intermediate member 136. A first end portion of intermediate member 136 is designated 146 and includes external threads formed thereon with the threads being designated 148. Intermediate member 136 further has a second end portion 150 on which are formed external threads 152.

Pressure relief valve 35 optionally but yet further preferably includes an external cap designated generally 154. Cap 154 includes an axial bore 156 formed therein and shown in dotted lines. Axial bore 156 has an internal bottom 158 shown in dotted lines in FIG. 15. Internal threads 160 within bore 156 are of the same size and pitch as external threads 152 on second portion 150 of intermediate member 136. This allows threaded engagement of cap 154 with intermediate member 136 when pressure relief valve 135 is in position within test block 23, as illustrated in FIG. 16. Knurled surface 155 formed about the upper cylindrical outer surface of external cap 154 facilitates manual rotation and removal of cap 154 portion from the remainder of pressure relief valve 35 when needed.

Referring to FIG. 15, and principally to FIG. 16 showing pressure relief valve 35 in position within test head 23, when pressure relief valve 35 is assembled, interior member 120, specifically the elongated central cylindrical portion 130 thereof, rides slidably within axial passageway 138 through intermediate member 136. Annular surface 128 formed on cylindrical end 122 of interior member 120 facingly contacts axially facing annular end surface 113 of cap 108. External threads 123 on end 122 of interior member 120 are of the same size, pitch and diameter as external threads 148 on first end portion 146 of intermediate member 136, with threads 123, 148 being of the same size facilitating threaded engagement of interior member 120 and intermediate member 136, with the internal threads 149 formed in the pressure relief valve chamber 42 in test head 23, as depicted in FIG. 16.

Still referring to FIGS. 15 and 16, recess 124 in first end 122 of interior member 120 is of cylindrical configuration and is sized to receive cylindrical cap 108 of valve stem 100.

When pressure relief valve 35 is in the assembled condition illustrated in FIG. 16 and external cap 154 is removed therefrom, elongated central cylindrical portion 130 of interior member 120 extends slidably through the length of axial passageway 138 in intermediate member 136 and protrudes from second end portion 150 of intermediate member 136, as can be visualized from FIG. 15. This permits manual rotation of interior member 120 using a hexagonal wrench fitting into hexagonal receptacle 134 formed in cylindrical second end 132 of interior member 120, illustrated in FIG. 15. As an operator manually rotates interior member 120 using a hexagonal "Allen" wrench, due to the interaction of threads 123 with threads 149, interior member 120 moves vertically up or down within and respecting test head 23, according to the direction of rotation.

Considering a view from the top of FIGS. 15 and 16, clockwise rotation of interior member 120 results in interior member 120 moving downwardly. Since interior member 120 is in sliding contact with valve stem 100, with the contact occurring between recess 124 in first end 122 of interior member 120 and surface 113 of cylindrical cap 108 of valve stem 100, clockwise rotation and resulting downward movement of interior member 120 moves cylindrical cap 108 of valve stem 100 downwardly, thereby compressing spring 106 and increasing the closure force applied by circular head 102 either to ball 119 or against valve seat 117, depending on whether ball 119 is present or not. This increased closure force results in a higher required hydraulic pressure to open pressure relief valve 35 with the pressure resulting from oil being present in passageways 81 and 42, as shown in FIG. 12. When pressure relief valve 35 opens due to oil pressure exceeding a preselected level, oil escapes from pressure relief valve chamber 42 and returns to oil sump 44 via diagonal duct 84, terminating in oil return port 54 shown in FIG. 5.

During normal operation, the portion of diagonal duct 84 to the right of pressure relief valve 35 in FIG. 5 is plugged. During fabrication, diagonal duct 84 is necessarily drilled in the direction shown in FIG. 5 due to the presence of the other ducts and structure within test block 33.

Further in the assembled condition, and again considering the view from the top looking down in FIGS. 15 and 16, clockwise rotation of intermediate member 136 results in downward movement of intermediate member 136, due to engagement of external threads 148 on first end portion 146 of intermediate member 136 with the internal threads 149 formed in pressure relief valve chamber 42. Intermediate member 136 may be further rotated clockwise until the external axially facing annular surface 142 on annular shoulder 140 facingly contacts an upwardly facing planar exterior surface 90 of test head 23 in which internally threaded pressure relief valve chamber 42 is formed, as illustrated in FIG. 16.

Once intermediate member 136 is rotated tightly into place, facing contact of external axially facing annular surface 142 of intermediate member 136 with the exterior surface 90 of test head 23, as shown in FIG. 16, provides a fluid-tight seal between pressure relief valve 35 and test head 23.

Once intermediate member 136 is in position with external axially facing annular surface 142 of intermediate member 136 in facing tight contact with the exterior surface of test head 23, oil can only escape around or through pressure relief valve 35 to the exterior of test head 23 by travelling through passageway 138 formed in intermediate member 136, which passageway is occupied by elongated central cylindrical portion 130 of interior member 120. Since there is sliding contact between the exterior of elongated central cylindrical portion 130 of interior member 120 and the interior surface of passageway 138 through intermediate member 136, a small amount of oil can seep between these two members. However, once threaded external cap 154 is screwed tightly into place on second end portion 150 of intermediate member 136, a fluid-tight seal is created and any oil seeping upwardly along the tiny clearance between the interior surface of passageway 138 through intermediate member 136 and the external surface of central cylindrical portion 130 of interior member 120 is blocked by the resulting fluid-tight seal between the annular exterior surface 162 formed around bore 158 in external cap 154 and the upwardly facing annular surface 153 formed on second end portion 150 of intermediate member 136.

Figure 17:
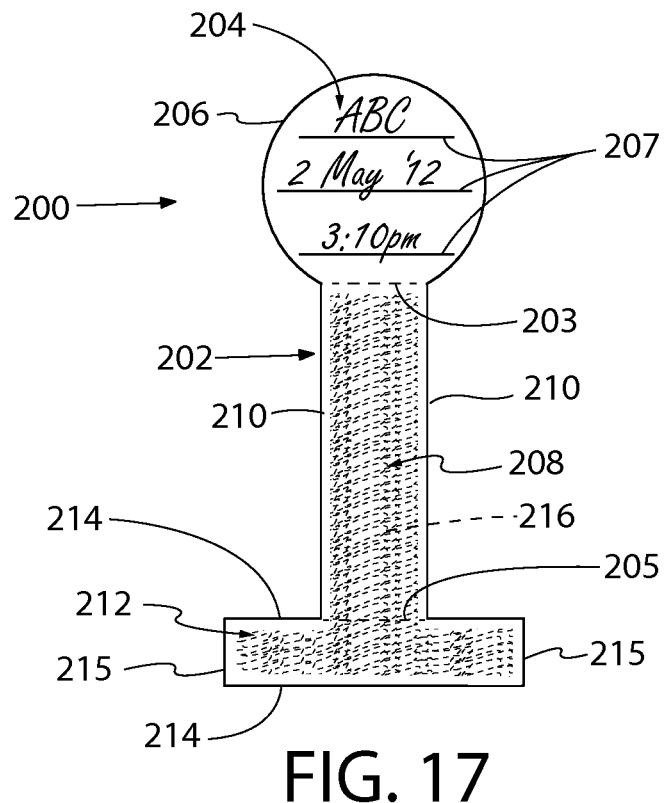
FIG. 17 is a plan view of one embodiment of a tamper indicator especially adapted for use with the pressure relief valve of the portable metal hardness tester illustrated in FIGS. 1 through 4 and 14.
Figure 18:
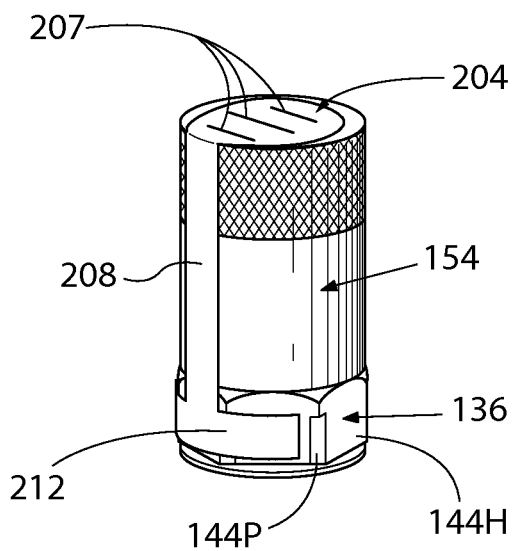
FIG. 18 is a isometric view of the optional but desirable external cap and an exposed part of the adjustable pressure relief valve illustrated in FIG. 15, in place in a test head of the portable metal hardness tester illustrated in FIGS. 1 through 4 and 14, showing tamper indicator tape affixed thereto.

FIGS. 17 and 18 illustrate a tamper detector portion of the portable Brinell metal hardness tester, where the tamper detector is depicted generally as 200 and includes a frangible sheet denoted 202. Sheet 202 includes a first portion 204 having a preferably circular periphery 206. A second portion of sheet 202 is denoted 208 with parallel, spaced apart edges of second portion 208 both being denoted 210. Sheet 202 further includes a third portion 212, where the parallel, spaced apart longitudinal edges of third portion 212 are both denoted 214 and the parallel, spaced apart end edges of third portion 212 are both denoted 215.

Tamper detector 200 further preferably includes adhesive 216, which has been denoted schematically in FIG. 17 as being on one side of sheet 202. In FIG. 17 adhesive 216 has been depicted as covering only a portion of tamper detector 200, namely the second and third portions 208 and 212, to enhance drawing clarity. However, it is to be understood that it is most desirable for adhesive 216 to cover one entire side of tamper detector 200 or even to be impregnated therein.

Sheet 202 may further include a crease 203, shown as a dotted line in FIG. 17, which may be a very narrow area, no wider than a pencil line, of reduced thickness or reduced strength, or both, or of perforate construction, thereby facilitating bending or folding of first portion 204 relative to second portion 208 of sheet 202. Sheet 202 may also desirably include a second crease 205, shown as a dotted line in FIG. 17, also desirably no wider than a pencil line, of reduced thickness or reduced strength or both, or of perforate construction, facilitating separation of third portion 212 from second portion 208.

First portion 204 of sheet 202 desirably includes lines 207 on which a test operator may place identifying information such as the test operator's initials, the date the tester was calibrated or the date the hydraulic fluid was changed, and the time of the calibration or change of hydraulic fluid. Lines for recording of such information thereon are indicated as 207 in FIG. 17, where exemplary information appears as would be written by an operator after either calibrating the tester or changing the hydraulic fluid, or both. Adhesive 216, or the adhesive side of sheet 202 if adhesive is impregnated therein, is preferably on the side of sheet 202 opposite from the side of sheet 202 an which lines 205 are located.

As further illustrated in FIG. 17, second portion 208 of sheet 202 has preferably parallel sides defined by edges 210 and preferably extends radially away from first portion 204. Third portion 212 of sheet 202 connects to second portion 208, preferably at a position defined by crease 205, remote from juncture of first portion 204 and second portion 208 as defined by crease 203. Third portion 212 includes longitudinally extending sides defined by edges 214 that are preferably parallel one with another, and ends 215 that are also preferably parallel one with another and desirably positioned at right angles to edges 214.

Referring to FIG. 18, when sheet 202 is positioned on external cap 154 and on intermediate member 136, adhesive 216 secures first portion 204 of sheet 202 to the circular outwardly facing top surface of external cap 154. Adhesive similarly secures second portion 208 of sheet 202 to the curved cylindrical side of external cap 154. Adhesive similarly secures third portion 212 of sheet 202 to one and preferably several of flat hexagonal panel surfaces 144H and to the flat surfaces 144P separating adjacent flat hexagonal panel surfaces 144H of intermediate member 136, all as illustrated in FIG. 18. With this arrangement, once sheet 202 is positioned and the adhesive has cured so that sheet 202 is bonded to external cap 154 and to intermediate member 136, a person cannot remove external cap 154 from threaded engagement with intermediate member 136 and the remainder of pressure relief valve 35 without fracturing sheet 202 at second crease 205 defining the juncture of second portion 208 and third portion 212. When an inspector sees a fracture of sheet 202 at crease 203 or proximate thereto, the inspector knows that someone has removed cap 154 and has likely tampered with pressure relief valve 35 of the metal hardness tester.

Sheet 202 may be paper or a polymer or any other suitable material. Sheet 202 preferably has one surface, opposite from the surface having adhesive 216 thereon that accepts ink or other writing media so that the operator may place identifying information on sheet 202, as shown in FIG. 17. Whatever material is chosen for sheet 202, the material must be frangible at crease 203 or proximate thereto so that an unauthorized person removing or attempting to remove external cap 154 from threaded engagement with intermediate member 136 will break sheet 202 at crease 203, thereby leaving evidence, namely the resulting break in sheet 202 of tampering with pressure relief valve 35. Frangibility at crease 203 is further important in that it allows first portion 204 to be removed by authorized personnel and retained as periodic evidence of tester calibration, hydraulic fluid changeover and the like.

Alternatively, adhesive 216 maybe supplied separately from sheet 202 and not coated on or impregnated therein. In such case, adhesive 216 is first applied to external cap 154 and intermediate member 136 of pressure relief valve 35. Sheet 202 is then marked with the appropriate time, date and operator identifying indicia, and adhered to cap 165 and intermediate member 136 of pressure relief valve 35 using adhesive 216. Providing space for the operator identifying indicia, date and time are optional.

Desirably, the circular periphery of 206 of first portion 202 is of lesser diameter than external cap 154, as illustrated in FIG. 18, to facilitate placement and fitting of sheet 202 on and around external cap 154 and intermediate member 136. Hence tamper detector 200 may be furnished in different sizes, to fit various sized and shaped versions of external cap 154 and intermediate member 136, and equivalents thereto.

Figure 3:
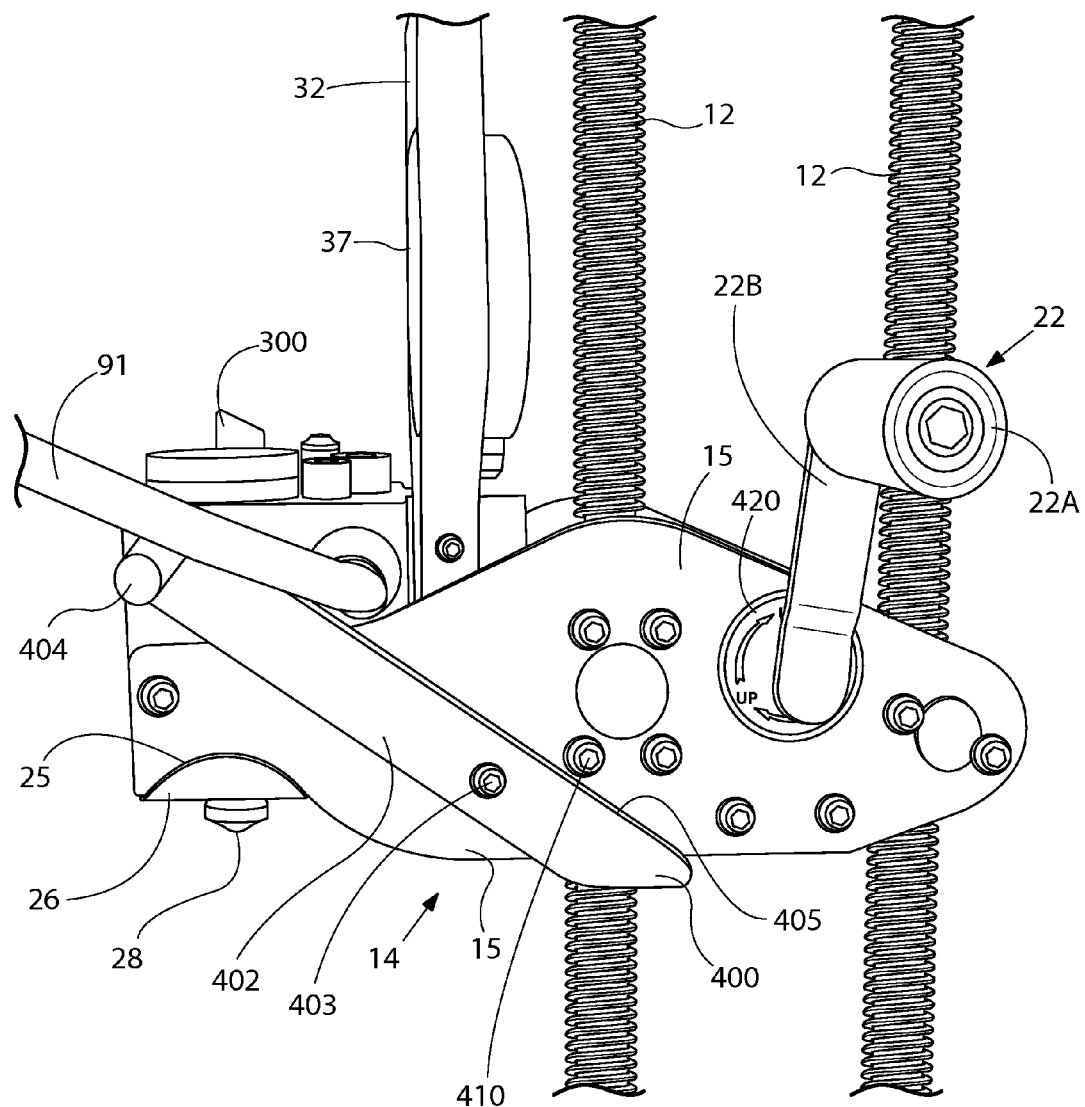
FIG. 3 is a broken right side elevation, similar to FIG. 2, but with the pumping lever contacting the pump stroke limiter, with the view taken from slightly left of center to provide depth to the drawing, thereby to enhance drawing clarity and ease of understanding.
Figure 19:
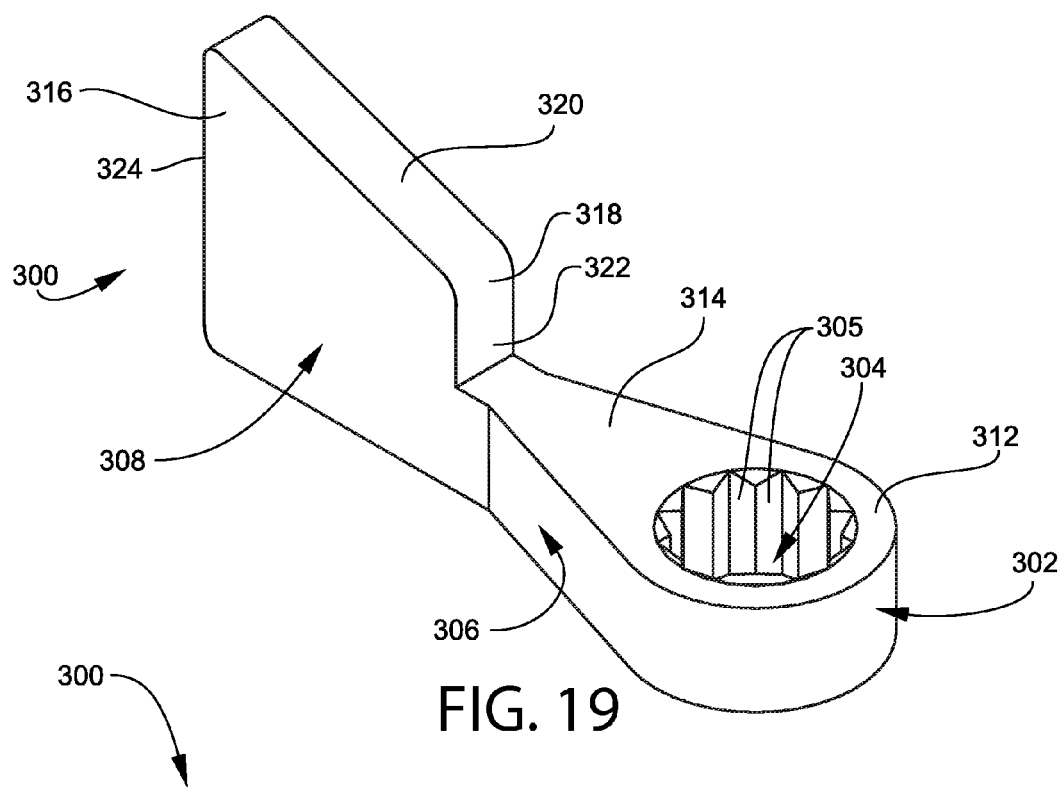
FIG. 19 is an isometric view of the top side, one side and one end of the handle for the pressure release valve of the portable metal hardness tester illustrated in FIGS. 1 through 4 and 14.
Figure 20:
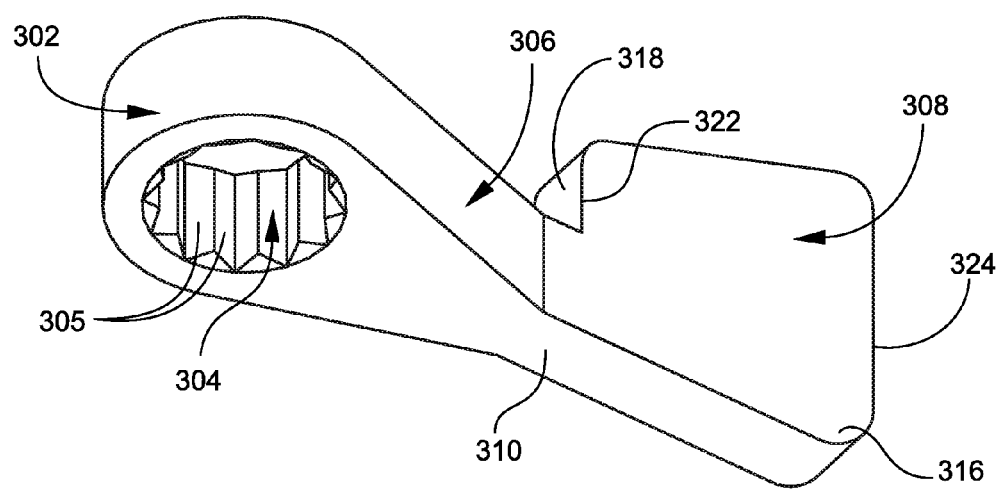
FIG. 20 is an isometric view of the bottom, the remaining side relative to that illustrated in FIG. 19, and the same end illustrated in FIG. 19 of the handle of the pressure release valve of the portable metal hardness tester illustrated in FIGS. 1 through 4 and 14.

FIGS. 19 and 20 are enlarged isometric views of pressure release valve handle 300 which is also at least partially visible in FIGS. 3, 4 and 14 of the drawings.

Referring to FIGS. 19 and 20, the pressure release valve handle is designated generally 300 and is used to open pressure release valve 36 to relieve hydraulic fluid pressure when desired from the reservoir and passageways in test head 23 shown in FIGS. 5, 12, and 13. Pressure release valve 36 connects with duct 82 as shown in FIG. 13; duct 82 connects with ducts 78 and 81 as shown in FIG. 12, which in turn connect with pressure relief valve chamber 42 and high pressure chamber 71, both also shown in FIG. 12.

Pressure release valve handle 300 preferably includes a ring-like portion 302 having an aperture 304 formed therein, with the aperture preferably being internally fluted, with the flutes being denoted 305 in FIGS. 19 and 20. Ring-like portion 302 with aperture 304 is sized for fitting over and receivingly gripping a rotatable shaft portion 303 of pressure release valve 36, which rotatable shaft portion extends externally of test head 23 at planar upper surface 90 thereof as is apparent from FIGS. 4 and 14. Pressure release valve handle 300 preferably further includes an intermediate portion 306 connecting to ring-like portion 302 and a blade portion 308 connecting to intermediate portion 306, remotely from ring-like portion 302. Blade portion 308 is of generally upstanding planar configuration and is preferably oriented in a co-planar relationship with an axis of shaft 303 of pressure release valve 36.

As best illustrated in FIG. 20, which is an isometric view in which the bottom surface of the pressure release valve handle 300 is visible, a lower or bottom surface of pressure release valve handle 300, designated 310, is preferably planar and extends and defines the entire lower surface of pressure release valve handle 300 when in place on the hardness tester. Planar lower surface 310 of pressure release valve handle 300 is flat for facing slidable contact with the upwardly facing planar exterior surface 90 of test head 23 as apparent from FIGS. 4 and 14.

As shown in FIG. 19, ring-like portion 302 and intermediate portion 306 of pressure release valve 300 preferably have planar upper surfaces 312, 314, which are parallel with planar lower surface 310. Blade portion 308 has width that is desirably less than the diameter of aperture 304. As illustrated in FIGS. 19 and 20, blade portion 308 preferably extends upwardly from planar lower surface 310 a greater distance than both intermediate portion 306 and ring-like portion 302. As further apparent from FIG. 19, intermediate portion 306 and ring-like portion 302 preferably extend upwardly from planar lower surface 310 a common distance.

As also evident from FIG. 19, a first part 316 of blade portion 308, which is remote from aperture 304, preferably extends upwardly from planar lower surface 310 a greater distance than a second part 318 of blade portion 308, which is more proximate to aperture 304. As further apparent from FIG. 19, a blade portion upper surface 320, which connects first and second parts 316, 318 of blade portion 308, is preferably a planar surface.

As further evident from FIG. 19 and from FIG. 20, blade portion 308 of pressure release valve handle 300 is preferably of uniform transverse thickness. As still further evident from FIG. 14, the common distance that intermediate portion 306 and ring-like portion 302 extend upwardly from planar lower surface 310 is preferably greater than the transverse thickness of blade portion 308. As still additionally evident from FIG. 19, blade portion 308 has a first vertically extending edge 322 adjacent to intermediate portion 306 and a second vertically extending edge 324 positioned at an extremity of blade portion 308 that is remote from ring-like portion 302. As shown in FIG. 19, second vertically extending edge 324 is preferably longer than first vertically extending edge 322.

The configuration of pressure release valve handle 300 and particularly the configuration of blade portion 308, with second vertically extending edge 324 extending upwardly a substantially greater distance than the thickness of ring-like portion 302, facilitates easy gripping of pressure release valve handle 300 between an operator's thumb and index finger. This permits the operator to easily actuate pressure release valve 36 and, if desired, to open pressure release valve 36 thereby releasing hydraulic pressure within the tester.

In the preferred embodiment, the pressure release valve handle 300 has a thickness of about one-eighth (⅛) of an inch. Blade portion 308 at its maximum height is preferably about three-quarters (¾) of an inch high. At the extremity of first vertically extending edge 322 of blade portion 308 remote from planar lower surface 310, the distance therefrom to planar lower surface 310 is preferably about one-half (½) of an inch. Height of the ring-like portion 302 and intermediate portion 306 measured from planar lower surface 310 is preferably about seven-sixteenths (7/16) of an inch.

Pressure release valve handle 300 is preferably formed from a single piece of aluminum machined to the shape shown in FIGS. 19 and 20.

Referring to FIGS. 1, 2 and 3, and particularly to FIG. 3, a stroke limiter designated generally 400, is adapted to be mounted on movable carriage 14 and includes a stop designated generally 404, which is connected to carriage 14 and positioned to contact the pump handle 91 at a predetermined limit of pump lever angular rotation, thereby to limit pump lever angular travel and thereby limit angular movement of the rotatable segmented gear 93, as illustrated in FIGS. 6, 9, 10, and 11, to a predetermined amount.

As shown in FIG. 3, stroke limiter 400 includes a strap 402 which is preferably an elongated piece of steel secured to side plate 15 by at least one bolt, numbered 403 in FIG. 3. Strap 402 is maintained in place by bolt 403 that passes through strap 402 and by contacting interference with an upper edge 45 of strap 402 and with an adjacent bolt 410, as illustrated in FIG. 3. Once bolt 403 passing through strap 402 is secured in place and strap 402 is positioned with upper edge 405 of strap 402 contacting bolt 410, strap 402 is immovable with respect to carriage 14.

Figure 10:
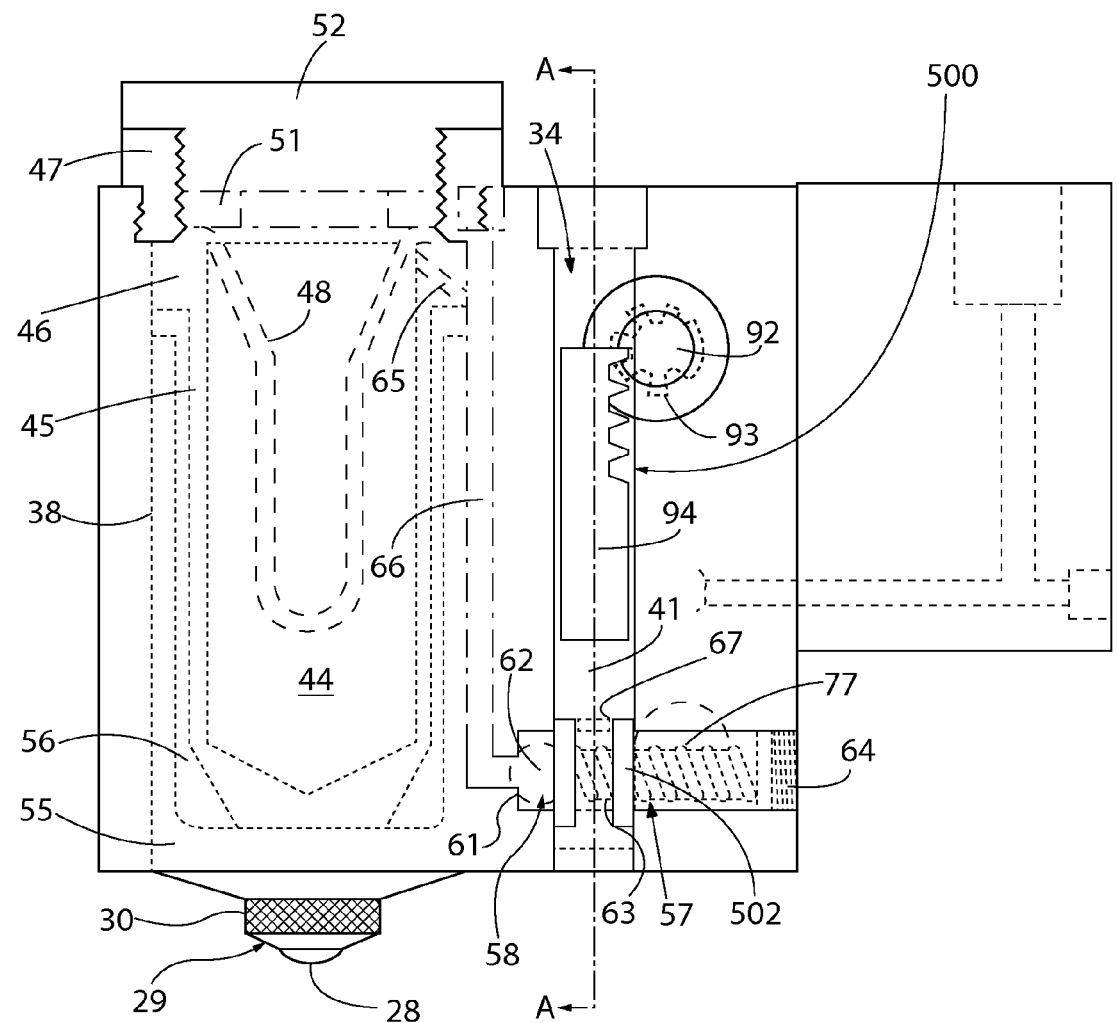
FIG. 10 is a right side elevation of the test head drawn similarly to FIG. 9 in partial section with the section taken at lines and arrows C-C in FIG. 5, with the pumping plunger 94, the stent 502, the pumping cylinder 41, and the low pressure valve chamber 58 all shown in heavy solid lines.
Figure 11:
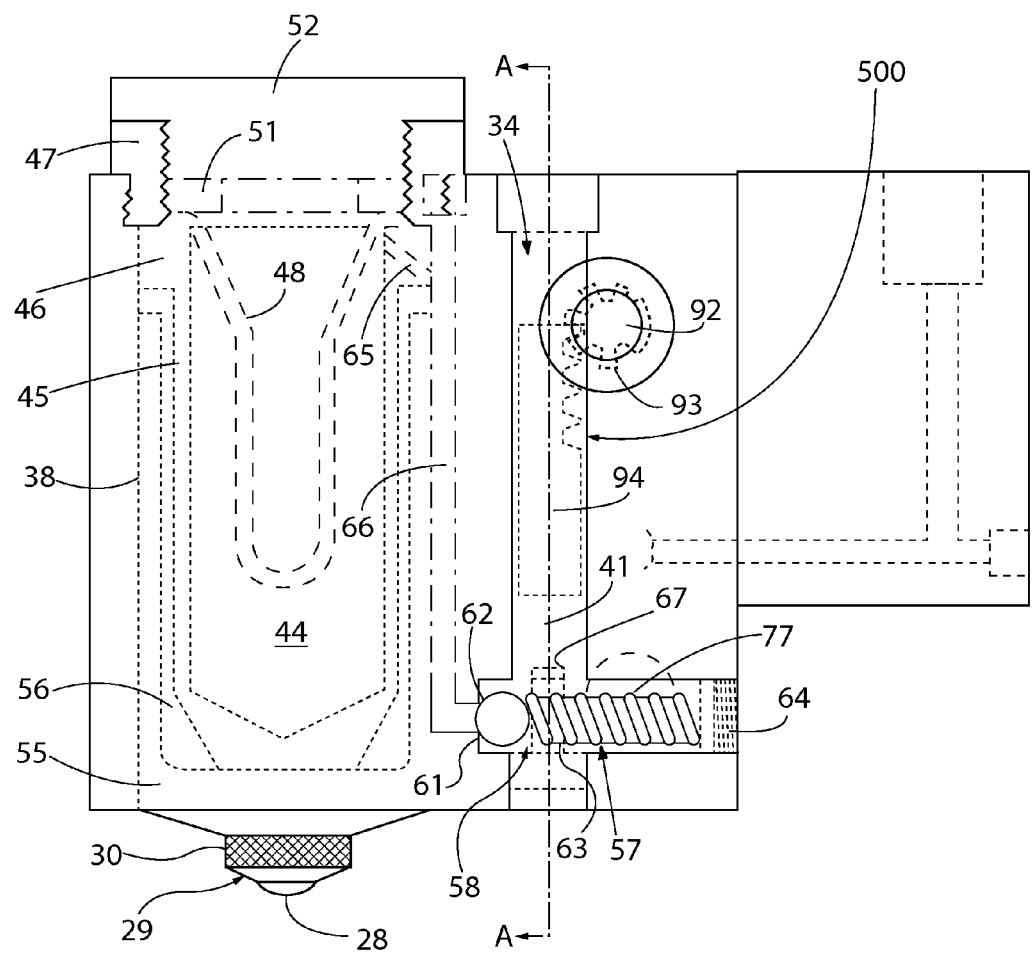
FIG. 11 is a right side elevation of the test head drawn similarly to FIGS. 9 and 10, in partial section similarly to FIG. 10 with the section taken at lines and arrows C-C in FIG. 5, with the pumping cylinder 41, the low pressure valve chamber 58, and the low pressure valve 57 all shown in heavy solid lines.

A pump lever travel limiting stop member 404 extends perpendicularly from strap 402 at a position proximate one end of strap 402. Pump lever travel limiting stop member 404 interferes with pump lever 91 upon pump lever 91 exceeding a preselected amount of angular travel from the starting position, at which segmented gear 93 engages the uppermost teeth of the rack portion of pump plunger 94 as illustrated in FIG. 10. Lever travel limiting stop member 404 is preferably cylindrical in form and secured to strap 402, with the axis of the cylinder being perpendicular to strap 402 and with lever travel limiting stop member 404 being in the same geometric plane in which pump lever 91 travels. With this arrangement, when pump lever 91 is brought to the preselected desired limit of angular travel, pump lever 91 contacts and interferes with lever travel limiting stop member 404, whereby further rotation of pump lever 91 is precluded. Lever travel limiting member 404 may be machined as a part of strap 402 or may be secured thereto by suitable machine screws.

A major advantage afforded by the portable Brinell metal hardness tester of this invention is that when the hardness tester test block 33 is fabricated, pumping cylinder 41 can be formed by drilling entirely through the block of metal from which test block 33 is formed. As apparent from FIGS. 6, 7, 8, 9, 10, and 11, pumping cylinder 41 is formed by drilling through the piece of metal eventually resulting as test block 33. This is to be contrasted to forming pumping cylinder 41 as a closed bottom bore or as a partially closed bottom bore, as is the case with some other portable Brinell metal hardness testers. Creating pumping cylinder 41 by straight through drilling through the chunk of metal resulting in test block 33 as the tester is fabricated provides substantial savings in manufacturing costs as contrasted to machining a closed bottom bore or partially closed bottom bore.

As shown in FIGS. 6, 7, 9, 10, and 11, pumping cylinder 41 intersects duct 77 within which a low pressure valve designated generally 57 resides. Low pressure valve 57 includes a ball check 62, biased closed by a spring 63, which is preferably a coil spring as illustrated and occupies the substantial axial length of duct 77. Duct 77 is closed at one end by cap screw 64.

The intersection of pumping cylinder 41 with duct 77 is clearly illustrated in FIGS. 6, 7, 8, 9, 10, and 11. With such intersection existing, reciprocating up-and-down movement of pumping plunger 94, as driven by manual rotation of segmented gear 93, could result in the lower extremity of pump plunger 94 contacting and damaging either spring 63, or ball check 57, or both, resident within duct 77. (The lower extremity of pump plunger 94 has not been numbered in the drawings, to enhance drawing clarity.)

To prevent contact between the lower extremity of pump plunger 94 and low pressure valve 57, a stent designated generally 502, is positioned at the intersection of pumping cylinder 41 and duct 77. Stent 502 is preferably tubular in form to fit in tight facing contact with the inner annular surface of pumping cylinder 41, as clearly illustrated in FIG. 8. Stent 502 includes a lateral recess designated generally 506 formed therein, with lateral recess 506 dimensioned and positioned to accommodate coil spring 63 of low pressure valve 57 as illustrated in FIG. 8.

Figure 8:
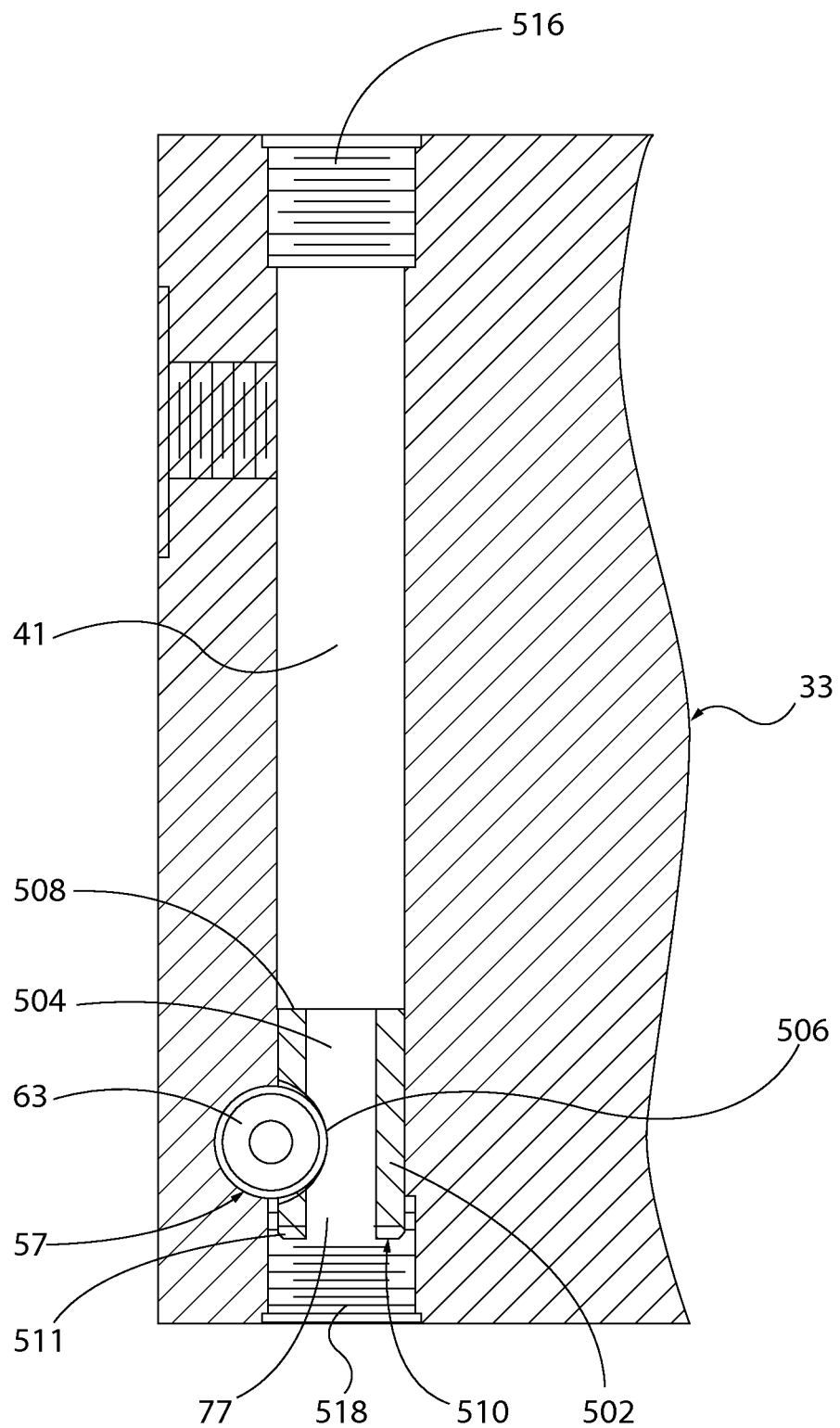
FIG. 8 is a partially broken sectional view of the test head taken at lines and arrows A-A in FIGS. 6, 9, 10, and 11.
Figure 9:
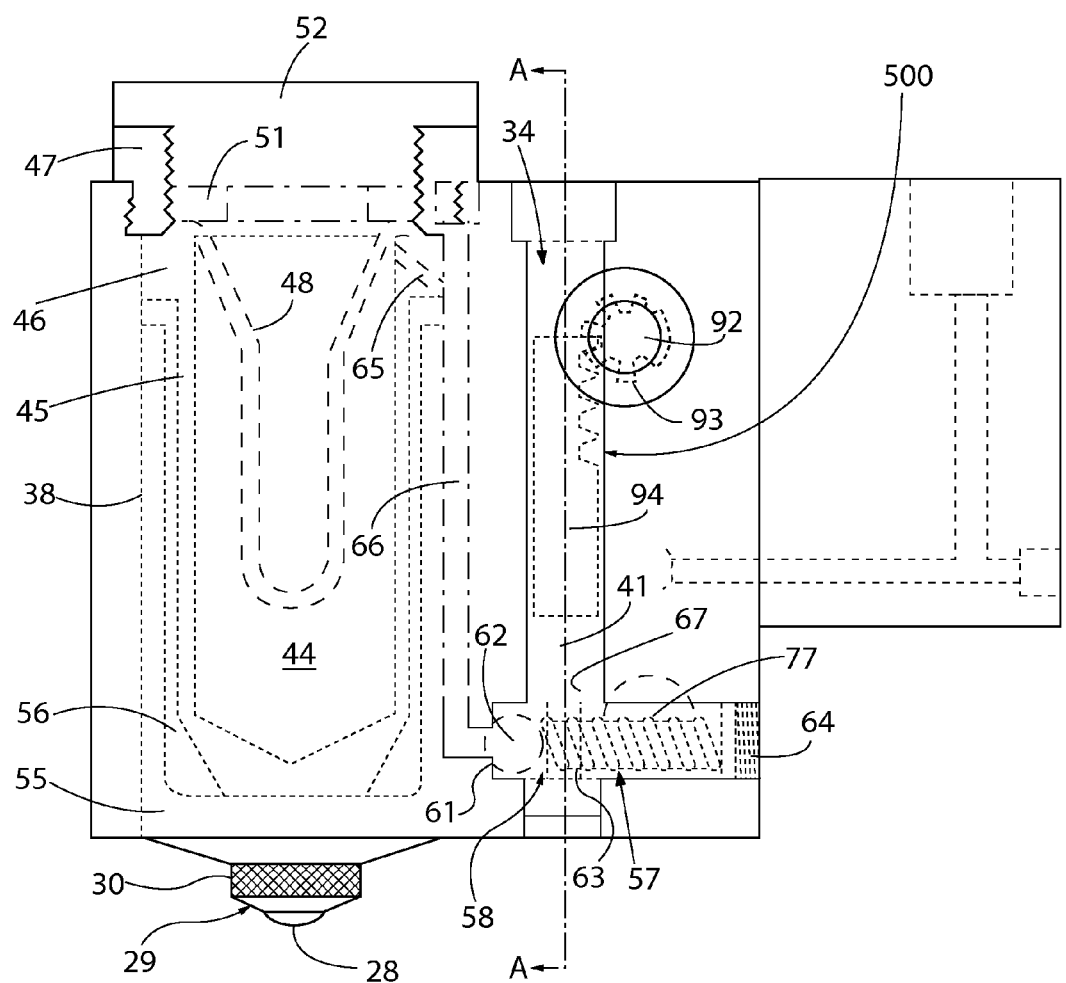
FIG. 9 is a right side elevation of the test head, drawn much the same as FIG. 6 but in partial section with the section taken at lines and arrows C-C in FIG. 5, with the dotted lines labeled "FIG. 7" removed, with certain other dotted lines also removed to enhance the clarity of the drawing, and with pumping cylinder 41 and low pressure valve chamber 48 shown in heavy solid lines.

An upper end of stent 502 is designated 508 in FIG. 8, while a lower end of stent 502 is designated 510 in FIG. 8. Stent 502 is preferably tubular and has an open center defining a passageway 504 through stent 502 for passage of hydraulic fluid pumped by the reciprocating action of pump plunger 94. Oil pumped by pumping plunger 94 passes around and through the center of coil spring 63 to reach aperture 61 leading to duct 66. Press fitting of stent 502 in place is preferable.

Lower end 510 of stent 502 has a transverse slot 511 found therein. Slot 511 is parallel with the center of lateral recess 506. When stent 502 is installed, transverse slot 511 is positioned transversely to the axis of spring 63, to position lateral recess 506 correctly to receive spring 63 therein. Slot 511 is visible in FIG. 8.

In the preferred embodiment of the invention, pumping cylinder 41 is preferably 2½ inches deep measured from the outer surface of test block 33 to the upper surface of stent 502 in FIG. 6. Stent 502 is preferably ⅝ inch in length in the axial direction parallel with pumping chamber 41. The openings in test block 33 defining either end of pumping chamber 41 are preferably counterbored and threaded to accept flat head machine screws so as to provide a flush, flat surface for the exterior of test block 33 around the openings. The interior surface of pumping cylinder 41 is preferably burnished to provide smooth, sliding contact for pumping rack 94 as it reciprocates within pumping cylinder 41.

As further illustrated in FIG. 3, the portable Brinell hardness tester is desirably equipped with elevator crank handle rotation indicators 420. These rotation indicators are desirably paper or polymer film, having adhesive on one side for attachment to the side plate 15 of carriage 14 about the shaft that is rotated by hand crank assembly 22 to raise and lower carriage 14. The elevator crank handle rotation indicators 420 include arrows showing the correct direction of hand crank assembly 22 in order to raise carriage 14 relative to base 11 of the tester. As illustrated in FIG. 3, the elevator crank handle rotation indicators and the arrow-like indicia together with the word "up" show that crank assembly 22 must be turned in the clockwise direction, viewing FIG. 3, in order to raise carriage 14 along elevating screws 12.

The test head 23 of tester 10 has many advantages. The passageways for the low and high pressure valves are preferably bored from a solid block so that there is no seepage around valve seat inserts. Moreover, the difficult and tedious job of setting valve seats is eliminated, unlike in prior art devices. The valve seats of previous devices had to be set perfectly or the oil would escape around the inserts and would lower the oil pressure leading to inaccurate readings.

The test head is easy to maintain. The essentially integral construction of test head 23 permits the use of heavy ball-check springs. Accordingly, pressure builds quickly, and there is little back flow of oil through the ball check valves. The strong springs enable the tester to hold the pressure once pressure has built up. In prior devices, dirt in the valve cylinders required removal of the valve seats for cleaning. But the fit of the valve seats was necessarily so close that such removal scored the valve cylinder walls, reducing the pressure of the device when the valve seats were replaced. In this tester, pressure is maintained more effectively because there are no valve block inserts and therefore there is no oil leakage around such valve block inserts.

Test head 23 is easy to construct because there are few ducts and holes, there are no inserts except for springs and valves, and tolerances need not be maintained particularly high. In test head 23, there are only two holes or ports between sump 44 and the wall of ram cylinder 38 and they are placed about 95° apart so that there is little chance of seepage. In the preferred embodiment, test head 23 weighs only about ten pounds so it is quite portable.

The following is claimed:

1. A portable Brinell metal hardness tester having a test head mounted in a movable carriage riding elevating screws, for applying preselected force to a test piece by manual pumping to apply hydraulic fluid pressure to a ball contacting the test piece, comprising:
   (a) a reciprocable pumping rack movable in response to movement of a pumping lever, for pumping hydraulic fluid into a passageway of the test head to increase hydraulic fluid pressure in the test head to a level required for metal hardness testing, wherein the rack is movable perpendicularly to the passageway;
   (b) a stent located in the passageway for pumped hydraulic fluid flow through the passageway into a test head of the tester to apply hydraulic fluid to the ball, the stent contacting and interferingly stopping the rack upon movement of the rack into the passageway by a preselected amount, wherein the stent is tubular and is co-axial with the passageway.

2. The Brinell metal hardness tester of claim 1 wherein the rack is movable vertically and the passageway is horizontal.

3. The Brinell metal hardness tester of claim 1 wherein the stent has a slot in one end.

4. The Brinell metal hardness tester of claim 1 wherein the stent has a lateral depression intersecting the stent interior.

5. The Brinell metal hardness tester of claim 4 wherein the depression is hemispherical.

6. The Brinell metal hardness tester of claim 5 wherein the depression is aligned with the rack.

7. A portable Brinell metal hardness tester, comprising:
   (a) a pumping rack movable in a fluid duct extending through a test head, for pumping hydraulic fluid from the duct into a passageway with which the duct communicates in the test head, to increase hydraulic fluid pressure in the test head to a level required for metal hardness testing, wherein the duct and the passageway are perpendicular to one another; and
   (b) a member positioned in the duct at the end thereof communicating with the passageway, the member halting movement of the pumping rack along the duct toward the passageway upon contact therewith, wherein the member is tubular and is co-axial with the passageway.

8. The hardness tester of claim 7 wherein the tubular member exterior facingly contacts the wall of the duct.

9. The hardness tester of claim 7 wherein the tubular member has open ends.

10. The hardness tester of claim 7 further comprising:
    (a) a check valve residing in the passageway at juncture with the duct;
    (b) the tubular member extending from within the duct into the passageway;
    (c) the tubular member having a recess formed therein receiving the check valve.

11. The hardness tester of claim 10 wherein the recess is a lateral recess.

12. The Brinell metal hardness tester of claim 7 wherein the rack is movable vertically and the passageway is horizontal.

13. The Brinell metal hardness tester of claim 7 wherein the tubular member has a slot in one end.

14. The Brinell metal hardness tester of claim 7 wherein the tubular member has a lateral depression intersecting an open interior of the tubular member.

15. The Brinell metal hardness tester of claim 14 wherein the depression is hemispherical.

16. The Brinell metal hardness tester of claim 15 wherein the depression is aligned with the rack.

* * * * *